(12) United States Patent
Summit et al.

(10) Patent No.: US 9,858,359 B2
(45) Date of Patent: *Jan. 2, 2018

(54) CONFORMAL HAND BRACE

(71) Applicant: 3D Systems, Inc., Rock Hill, SC (US)

(72) Inventors: Scott Summit, Mill Valley, CA (US); Kenneth B. Trauner, San Francisco, CA (US); Andrew R. Miller, Oakland, CA (US); Andrew Zukoski, Berkeley, CA (US); Robert P. Vallone, Palo Alto, CA (US)

(73) Assignee: 3D SYSTEMS, INC., Rock Hill, SC (US)

( * ) Notice: Subject to any disclaimer, the term of this patent is extended or adjusted under 35 U.S.C. 154(b) by 963 days.

This patent is subject to a terminal disclaimer.

(21) Appl. No.: 13/955,951

(22) Filed: Jul. 31, 2013

(65) Prior Publication Data

US 2013/0317788 A1 Nov. 28, 2013

Related U.S. Application Data

(63) Continuation-in-part of application No. PCT/US2012/051612, filed on Aug. 20, 2012, which is a continuation-in-part of application No. 13/214,096, filed on Aug. 19, 2011, now abandoned, which is a continuation-in-part of application No. 12/820,968, filed on Jun. 22, 2010, now abandoned, which is a continuation-in-part of application No. 12/615,196, filed on Nov. 9, 2009, now Pat. No. 8,005,651.

(Continued)

(51) Int. Cl.
*G06F 17/50* (2006.01)
*A61F 5/01* (2006.01)
*A61F 5/02* (2006.01)

(52) U.S. Cl.
CPC ............... *G06F 17/50* (2013.01); *A61F 5/01* (2013.01); *A61F 5/013* (2013.01); *A61F 5/0118* (2013.01); *A61F 5/0123* (2013.01); *A61F 5/02* (2013.01)

(58) Field of Classification Search
CPC combination set(s) only.
See application file for complete search history.

(56) References Cited

U.S. PATENT DOCUMENTS 5,810,753 A * 9/1998 Eberbach .............. A61F 5/0118
602/20
5,880,964 A * 3/1999 Schall .................. A61F 2/5046
623/27

(Continued)

OTHER PUBLICATIONS

PCT International Search Report of the International Searching Authority for International Application No. PCT/US2014/025615, mailed Mar. 13, 2014 (4 pages).

(Continued)

*Primary Examiner* — Aniss Chad
(74) *Attorney, Agent, or Firm* — Staniford Tomita LLP

(57) ABSTRACT

A conformable hand brace includes inner surfaces for supporting thumb and palm portions of a patient's hand and an adjustable mechanism that allows the cross section of the brace to be adjusted. The design of the conformal hand brace can be automatically designed by a computer based upon anatomical measurements of a patient's hand derived from a plurality of photographs of the hand.

18 Claims, 18 Drawing Sheets

Related U.S. Application Data

(60) Provisional application No. 61/799,361, filed on Mar. 15, 2013, provisional application No. 61/112,751, filed on Nov. 9, 2008, provisional application No. 61/168,183, filed on Apr. 9, 2009, provisional application No. 61/185,781, filed on Jun. 10, 2009.

(56) References Cited

U.S. PATENT DOCUMENTS

| | | | |
|---|---|---|---|
| 7,340,316 B2* | 3/2008 | Spaeth | A61B 5/0064 700/182 |
| 2004/0068337 A1* | 4/2004 | Watson | A61F 2/5046 700/98 |
| 2005/0015172 A1* | 1/2005 | Fried | G06F 19/3437 700/118 |
| 2006/0100832 A1* | 5/2006 | Bowman | A61F 2/5046 703/2 |
| 2007/0225630 A1* | 9/2007 | Wyatt | A61F 5/0118 602/21 |
| 2008/0319362 A1* | 12/2008 | Joseph | A61F 5/01 602/7 |
| 2010/0138193 A1* | 6/2010 | Summit | G06F 17/50 703/1 |
| 2010/0262054 A1* | 10/2010 | Summit | G06F 17/50 602/14 |
| 2011/0301520 A1* | 12/2011 | Summit | A61F 5/01 602/16 |

OTHER PUBLICATIONS

PCT Written Opinion of the International Search Authority for International Application No. PCT/US2014/025615, mailed Mar. 13, 2014 (5 pages).

* cited by examiner

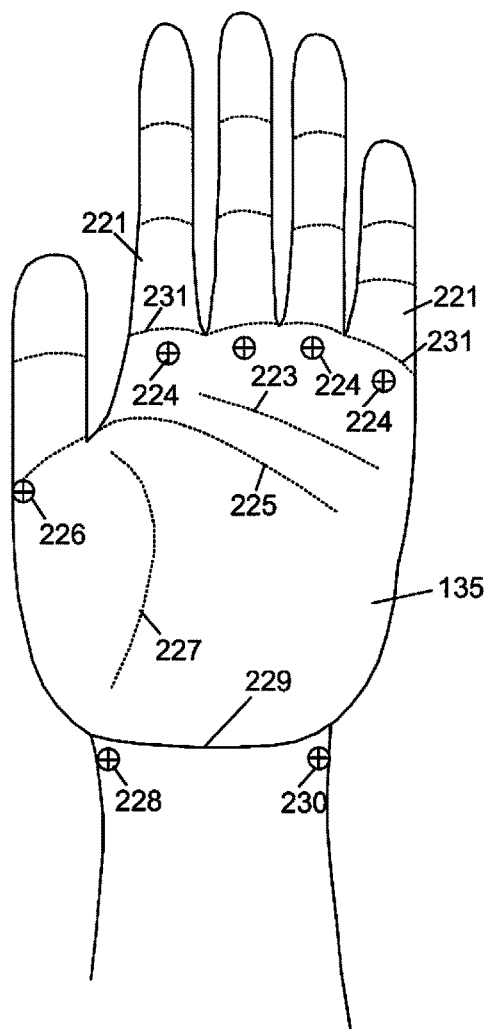
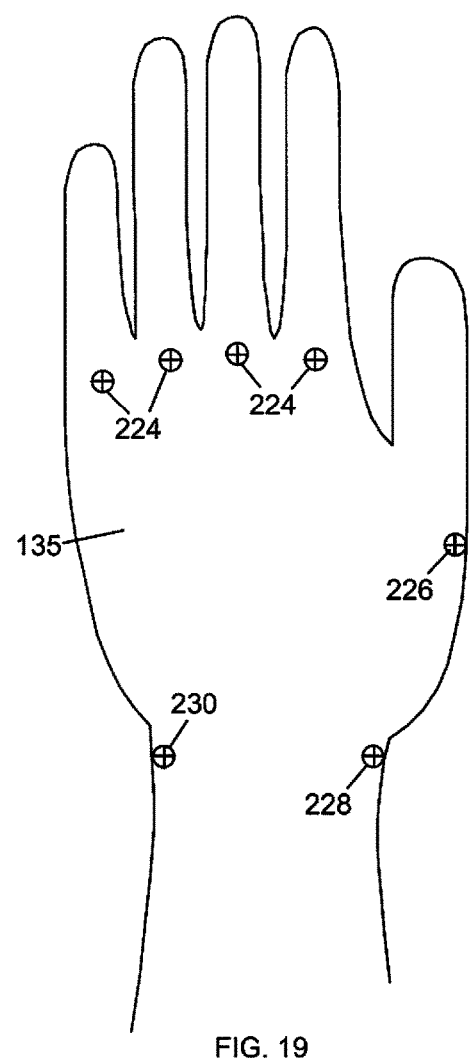
FIG. 18
FIG. 19

CONFORMAL HAND BRACE

CROSS REFERENCE TO RELATED APPLICATIONS

This application claims priority to U.S. Provisional Application No. 61/799,361, "Conformal Hand Brace" filed Mar. 15, 2013 and PCT Application No. PCT/US12/51612, "Adjustable Brace" filed Aug. 20, 2012 which claims priority from U.S. patent application Ser. No. 13/214,096, "Adjustable Brace" filed Aug. 19, 2011 which is a continuation-in-part of U.S. patent application Ser. No. 12/820,968, "Modular Custom Braces, Casts And Devices And Methods For Designing And Fabricating filed Jun. 22, 2010 which is a continuation-in-part of U.S. patent application Ser. No. 12/615,196, now U.S. Pat. No. 8,005,651, "Custom Braces, Casts and Devices And Methods For Designing And Fabricating" filed Nov. 9, 2009 which claims priority to U.S. Provisional Patent Application No. 61/112,751, "Brace And Cast" filed on Nov. 9, 2008, U.S. Provisional Patent Application No. 61/168,183, "Orthopedic Braces" filed in Apr. 9, 2009, and U.S. Provisional Patent Application No. 61/185,781, "Bespoke Fracture Brace" filed in Jun. 10, 2009. The contents of PCT Application No. PCT/US12/51612 and U.S. patent application Ser. Nos. 13/214,096, 12/820,968, 12/615,196, 61/375,699, 61/112,751, 61/168,183, and 61/185,781 are hereby incorporated by reference in their entirety.

BACKGROUND

A problem with hand braces is that they can be fabric covered devices that are uncomfortable to wear and unattractive to look at. Many braces have padding that is secured around the hand with Velcro straps and a rigid structure that prevents the brace from moving which immobilizes the hand. The fabric and padding can absorb sweat and other liquids that can cause stains and the brace may need to be washed periodically. Because of these issues, many patients tend to not wear hand braces. What is needed is an improved and simplified brace that is easily placed on the patient's body, thin, lightweight, comfortable to wear and more attractive than existing braces.

SUMMARY OF THE INVENTION

The present invention is directed towards a conformal hand brace. In an embodiment, the conformal hand brace can be an apparatus having a palmar surface that conforms or closely corresponds to a digital representation of the palmar surface of the patient's hand. The conformal hand brace can include a thumb section that surrounds a portion of the thumb. The length of the thumb section can be as long as necessary to provide the required support for the patient's thumb. If the thumb does not need support, the thumb portion can be very short. In contract, if the thumb needs to be immobilized, the thumb section can surround most or all of the thumb. The conformal hand brace can extend around the small finger and thumb sides of the hand. The back of the conformal hand brace can have an open section that allows a patient to place the brace on the hand or remove the brace from the hand.

A band can be attached to the back of the conformal hand brace and extend across the open section. The inventive hand brace can be adjusted to proper size so that the patient's injured hand is properly supported. The band can have a plurality of different settings with each setting providing a different circumferential geometry and brace tension. By adjusting the adjusting the band setting, the patient can obtain the proper or most comfortable hand brace tension. For example, if the patient's hand is swollen the band can be set to a looser setting.

The inner surface of the conformal hand brace can correspond to a digital representation of the hand of the patient. In an embodiment, the digital representation can be obtained by taking a plurality of digital photographs of the patient's hand. One or more colored stickers can be applied to the patient's hand and a plurality of markings or points of visible or IR light can be projected to the patient's hand. The hand can then be photographed by a plurality of infrared (IR) or visible light cameras. From the photographs, a three dimensional digital representation of the limb can be created by photogrammetry, image correlation, depth mapping or any other suitable IR and/or visible light photography based surface topography detection method. From the three dimensional representation of the hand surface topography, an adjustable brace can be designed having an inner surface that corresponds to the three dimensional digital representation of the patient's arm and hand. The inner surface of the brace and design can be asymmetrically offset from the digital representation of the patient's arm and hand. For example, a first portion of the brace can have a thumb section that has a first offset, a lateral back of hand portion that has a second offset and a palmar portion that has a third offset. The first offset may be less than the second offset which can be less than the third offset. The offsets can be positive or negative in relation to the principle digital representation of the arm. In the case of a positive offset, the offset is raised above the principle digital representation of the arm in the region of the offset. In the case of a negative offset, the offset is lowered below the principle digital representation of the arm in the region of the offset.

The inventive custom design process is unique because it provides a virtual fitting of the brace to the patient prior to fabrication of the actual device. No other known system provides the ability to automatically design custom adjustable braces in a virtual manner based upon anatomical feature measurements obtained photographically. In particular, the inventive process can detect markings placed on a body and utilize this information to design the adjustable brace based upon the measured locations of the marks. In an embodiment, the inventive system and method can be used by a computer to automatically design the conformal hand brace based upon anatomical measurements.

In an embodiment, the brace or cast has a smooth inner surface that conforms and corresponds to the digital representation of the scanned surface of the limb. Because the inner surface of the brace accurately conforms to the patient to provide a very close fit, the surface of the limb matches the inner surface of the brace. In some embodiments, the proper fit may not exactly match the digital representation of the limb. In order to provide a proper fit, the inner surface of the brace can be slightly larger or smaller than the surface data of the limb which can provide a looser or tighter fit on the hand. Because the inner surface of the brace corresponds to the digital representation of the limb, the brace can be worn by the patient without any padding. The brace can be made of a hard plastic material and the inner surface of the brace should also be very smooth. In order to be comfortable, the inner surface can have a surface finish of less than of less than 500 $R_a\mu$ inch. A brace or cast that can be worn by a patient without padding has several benefits including:

simplified brace design and construction, less weight, lower profile, better ventilation, no absorption of water, easier cleaning, etc.

BRIEF DESCRIPTION OF THE DRAWINGS

FIG. 18 illustrates a palmar view of a hand with markings;

FIG. 19 illustrates a dorsal view of a hand with markings;

DETAILED DESCRIPTION

The present invention is a custom designed and adjustable conformal hand brace having interior surfaces that corresponds closely to a digital representation of a patient's hand which can be obtained from an optical scan of the patient. The adjustable brace can be designed to closely fit around the hand with a palmar support surface and support surfaces for the sides of the hand. The back of the hand can be open to allow the conformal hand brace to be placed onto or removed from the hand. A band can be extend across the open section of the back of the conformal hand brace. The band of the conformal hand brace can be adjusted to accurately fit the patient's anatomy as the surface changes.

Figure 1:
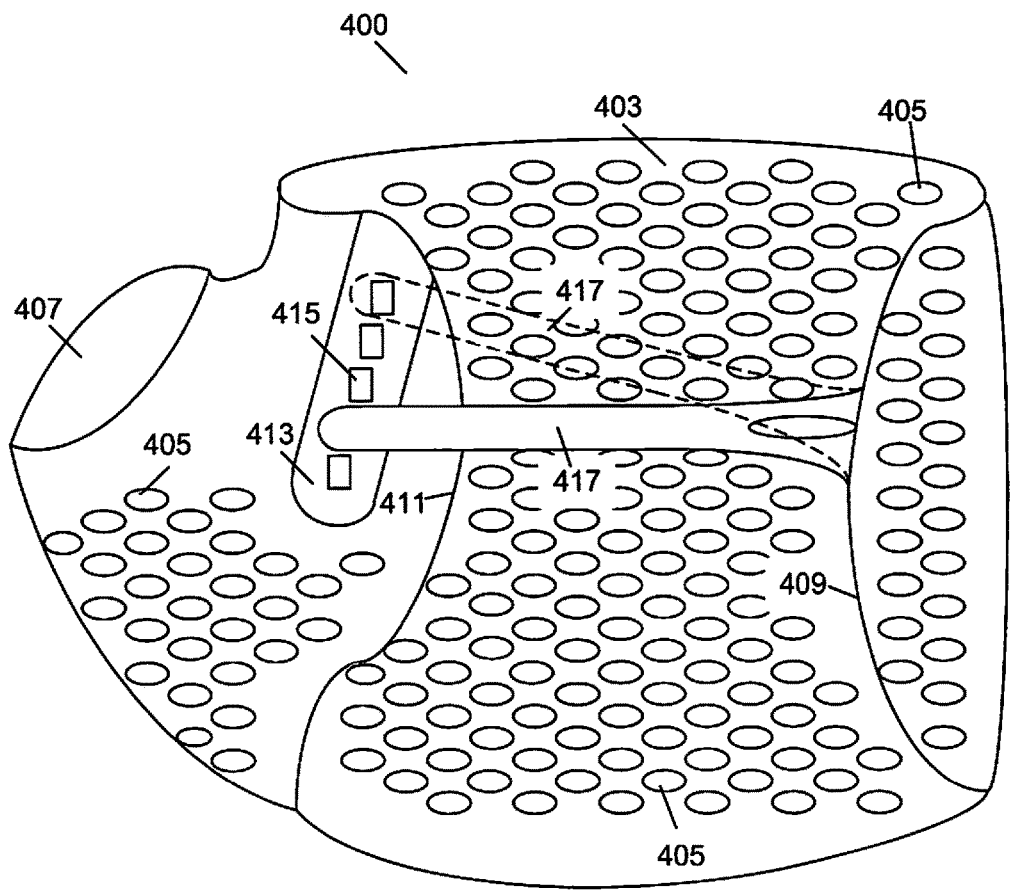
FIG. 1 illustrates a top view of an embodiment of an adjustable hand brace.

With reference to FIG. 1, a top view of an embodiment of an adjustable hand brace 400 is illustrated. The adjustable hand brace 400 can include an inner surface 403 and a thumb hole 407 that correspond to a digital representation of a patient's hand that can be obtained from optical photographs. The inner surface 403 will normally have both concave areas such as the areas surrounding the sides of the hand as well some convex surfaces that can correspond to concave portions of the body such as the palms. The adjustable brace 400 can also have a plurality of ventilation holes 405 which allow air to circulate around the patient's hand. An adjustment member 417 can be attached to one edge 409 of the hand brace 400 and one or more adjustable fastener holes 415 can be attached to or formed in the brace 400 adjacent to the second edge 411 on the opposite side of the brace 400. In an embodiment, the one or more adjustable fastener holes 415 can be formed in a raised portion 413 of the brace 400 that is thicker than some or all of the other areas of the brace 400. This thicker portion 413 can provide additional physical strength and can help to keep the adjustable fastener away from the patient's hand. When the brace 400 is placed on the patient, the thumb is placed through the thumb hole 407 and the palm is placed against the inner surface 403. The adjustable member 417 is a flexible structure that can be moved through a wide range of different positions.

Figure 2:
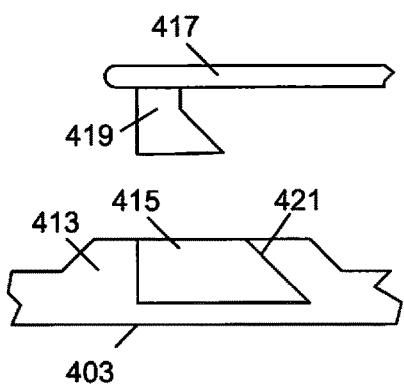
FIGS. 2 and 3 illustrate cross section side views of an embodiment of the adjustment member and an adjustable fastener hole.
Figure 3:
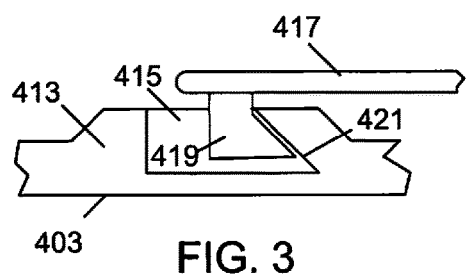

With reference to FIGS. 2 and 3, a side view of an embodiment of the adjustment member 417 and an adjustable fastener hole 415 is illustrated. To secure the brace 400 around the hand, a hook 419 at the end of the adjustable member 417 can be manually pulled to the desired tension and placed over the corresponding hole 415 as shown in FIG. 2. The hook 419 is then placed into the hole 415 as shown in FIG. 3 and the adjustable member 417 can be released. The tension on the adjustable member 415 will cause the hook 419 to engage the corresponding angled surface 421 within the hole 415 and hold the adjustable member 417 to the hole 415. The patient can also release the hook 419 from the hole 415 by pulling upon the end of the adjustable member 417.

In an embodiment, as illustrated in FIG. 1, the plurality of fastener holes 415 can be configured in different distances from the second edge 411 to allow the adjustable member 417 to control the cross section of the brace 400. Thus, the adjustable member 417 can be moved horizontally over the holes 415 until the hook 419 is placed over the proper hole 415 that provides the desired tension. The hook 419 can then be placed in the hole 415 so that the adjustable member 417 will be secured in place. In this case, the holes 415 towards the finger end of the brace 400 are closer to the second edge 411 and will produce a looser fit and the holes 415 towards the wrist section of the brace 400 are farther from the second edge 411 and will produce a tighter fit. In other embodiments, the holes 415 can be arranged in any other configuration that provides multiple adjustable member 417 settings. The brace 400 can be adjusted by the patient as the hand expands and contracts due to changes in temperature, atrophy, or swelling due to injury.

Figure 4:
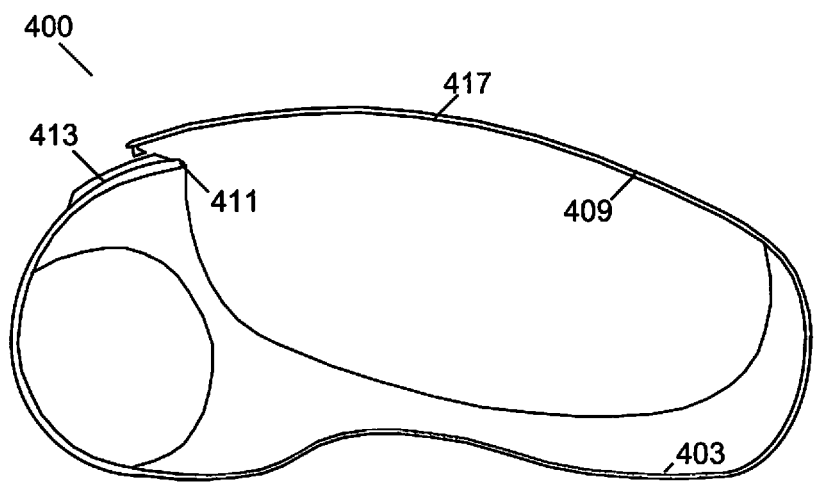
FIGS. 4 and 5 illustrate side views of an embodiment of an adjustable hand brace.
Figure 5:
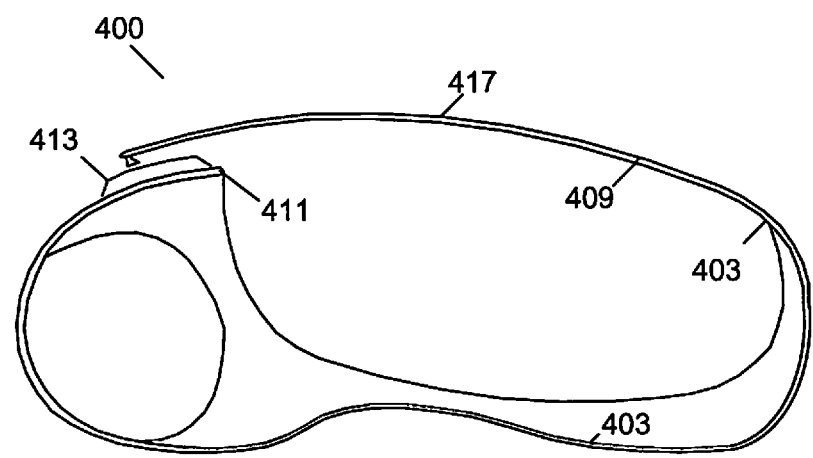

With reference to FIGS. 4 and 5, side views of the brace 400 illustrate how the cross sectional area changes by altering the adjustable member 417 placement. With reference to FIG. 4, the patient may start wearing the brace 400 in an expanded position with the hook 419 of the adjustable member 417 in one of the plurality of holes 415 that is closer to the second edge 411 producing a looser fit. Over time the patient's hand may decrease in size due to reduced swelling and/or atrophy and the brace 400 may need to be contracted to provide a proper fit. With reference to FIG. 5, the cross sectional area of the brace 400 can be reduced by moving the hook 419 to a hole 415 that is farther from the second edge 411 to produce a better fit on the patient's hand as the hand shrinks in size. The patient can continue to adjust the adjustable member 417 to obtain the best fit as size of the hand changes.

Figure 6:
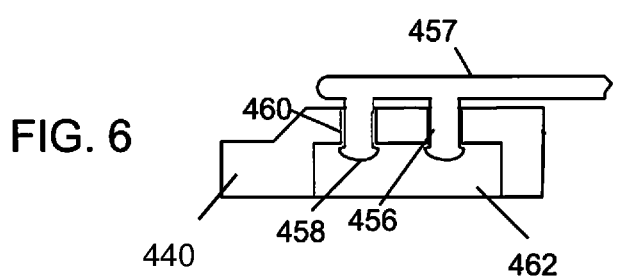
FIG. 6 illustrates a cross section side view of a portion of an embodiment of an adjustable member coupled to a brace.

In an embodiment, the adjustable member 457 can be created as an integrated portion of the brace 440 (such as the adjustable member 417 of FIG. 1 is an integrated portion of the brace 400). For example, if the brace 440 is fabricated using a 3D printing machine, the adjustable member 457 is formed with the brace 440 as a single integrated structure. However, in other embodiments, the adjustable member 457 can be a separate component that is attached to the brace 440 but may not be an integrated part of the brace structure. With reference to FIG. 6 a cross section view of a portion of an embodiment of the brace 440 is illustrated. The illustrated embodiment of the adjustable member 457 can be a separate structure that includes one or more fastening pins 456 that have flared tips 458 and are placed through holes 460 in the brace 440. The diameter of the pins 456 can be smaller than the diameter of the holes 460 but the outer diameter of the tips 458 can be larger than the diameter of the holes 560. By pressing the flared tips 458 through the holes 460, the adjustable member 457 is secured to the brace 440. The brace 440 can have a recessed portion 462 so that the tips 458 are above the inner surface of the brace 440. This design also allows the adjustable member to be replaced if necessary. For example, the adjustable member 457 may break or a different length adjustable member can be used to provide a better fit on the patient. In an embodiment, the adjustable member can be stocked in various lengths and attached to the brace 440 after it has been fabricated.

Figure 7:
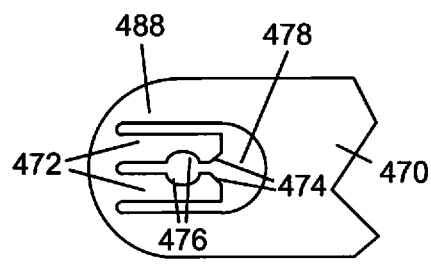
FIG. 7 illustrates a top view of a portion of an embodiment of an adjustable member of the brace.
Figure 8:
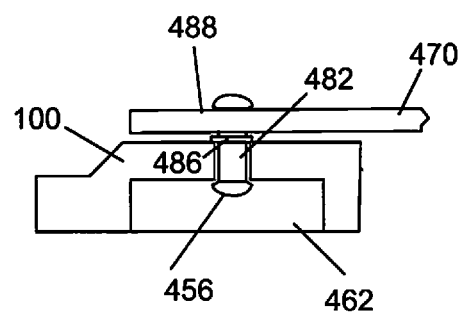
FIG. 8 illustrates a cross section view of a portion of an embodiment of an adjustable member coupled to a brace.

FIGS. 7 and 8 illustrate another connection mechanism for coupling the adjustable member 470 to the brace 100. In this embodiment, the end of the adjustable member 470 can have a clip mechanism 488 at one end and a hook 419 at the opposite end as illustrated in FIGS. 2 and 3. The clip mechanism 488 can include two elongated prongs 472 that have tapered ends 474 and clip holding sections 476. The ends of the prongs 472 can be coupled to the adjustable member 470 and may be flexible to allow for some elastic deflection. The clip mechanism 488 can also have an open space 478 adjacent to the tapered ends 474. The clip mechanism 488 can be clamped around a pin 482 having flared tips 458 at the ends and a center flange 490. The pin 482 can be inserted into a hole in the brace 100 having an inner diameter that is smaller than the outer diameter of the flared tip 458 and the lower flared tip 458 can extend into a recessed portion 462. The flange 486 can rest against the outer surface of the brace 100 to keep the upper portion of the pin 482 extending away from the brace 100. The upper portion of the pin 482 can be placed into the open space 478 and clip mechanism 488 can be moved around the pin 482 so the prongs 472 spread apart and slide under the upper flared tip 458 until the upper portion of the pin 482 is positioned within the clip holding sections 476 of the prongs 472. The clip holding sections 476 of the prongs 472 will hold the clip mechanism 488 in place on the pin 482.

Figure 9:
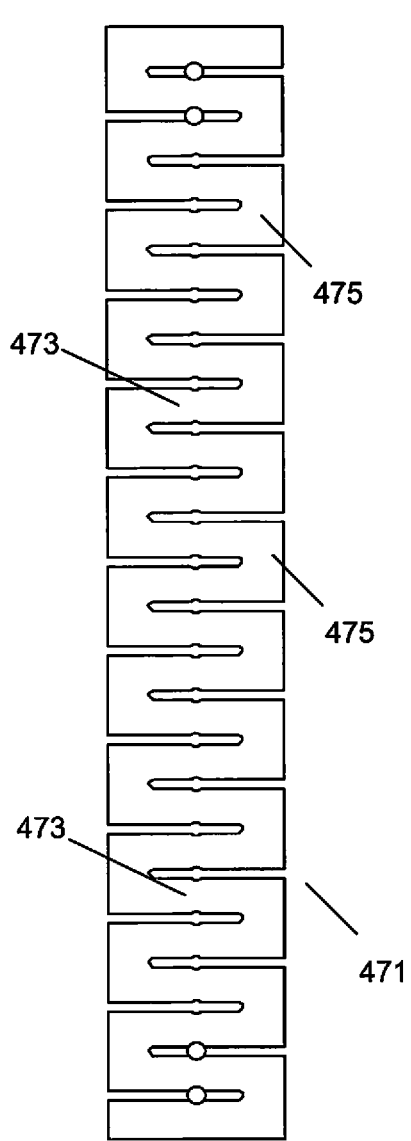
FIGS. 9 and 10 illustrate top views of an embodiment of an elastic adjustable member.
Figure 10:
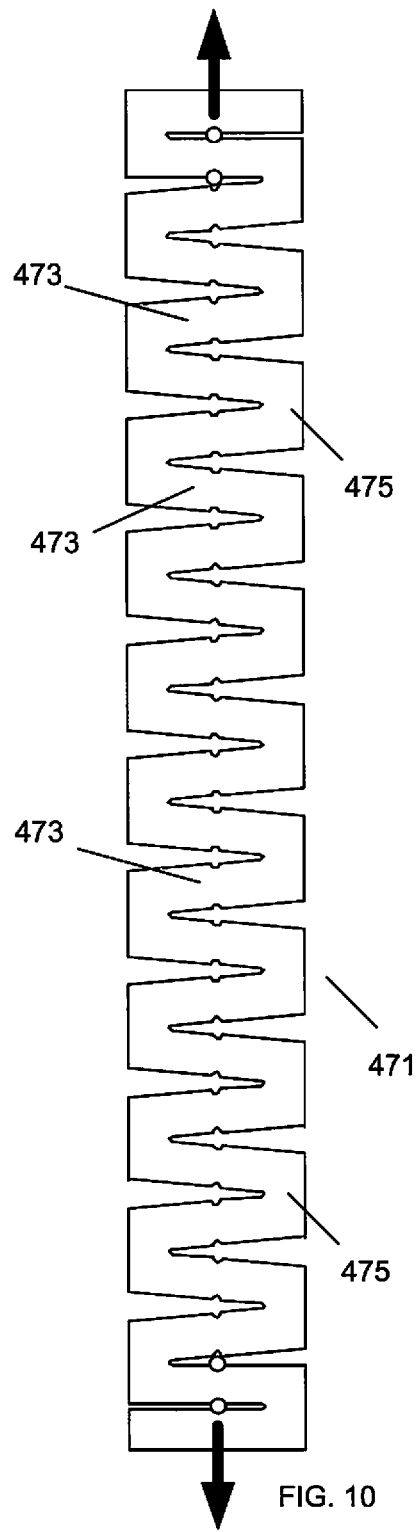

Because the adjustable member 457 can be a linear structure that is made of a relatively inelastic material, the adjustable member 457 may not stretch. Thus, the tension will change if the portion of the limb surrounded by the adjustable member 457 changes due to swelling or shrinking. In other embodiments, it may be desirable to secure the brace 100 to the limb with an elastic adjustable member that can vary in length. For example with reference to FIG. 9, an embodiment of an elastic member 471 in a normal compressed state is illustrated. In this embodiment, the elastic member 471 has a serpentine shape that has a plurality of members 473 that are substantially perpendicular to the length of the elastic member 471. The ends of the members 473 can link the adjacent connectors 475 and run parallel to the length of the elastic member 471. With reference to FIG. 10, when tension is applied to the elastic member 471, the connectors 475 can elastically bend which allows the elastic member 471 to stretch in length. When stretched, the members 473 can be angled so that they are no longer parallel to each other. When the tension is released, the elastic member 471 will return to its original shape as shown in FIG. 9. Securing the brace to limb with the elastic member 471 can provide a more comfortable fit for the patient.

Figure 11:
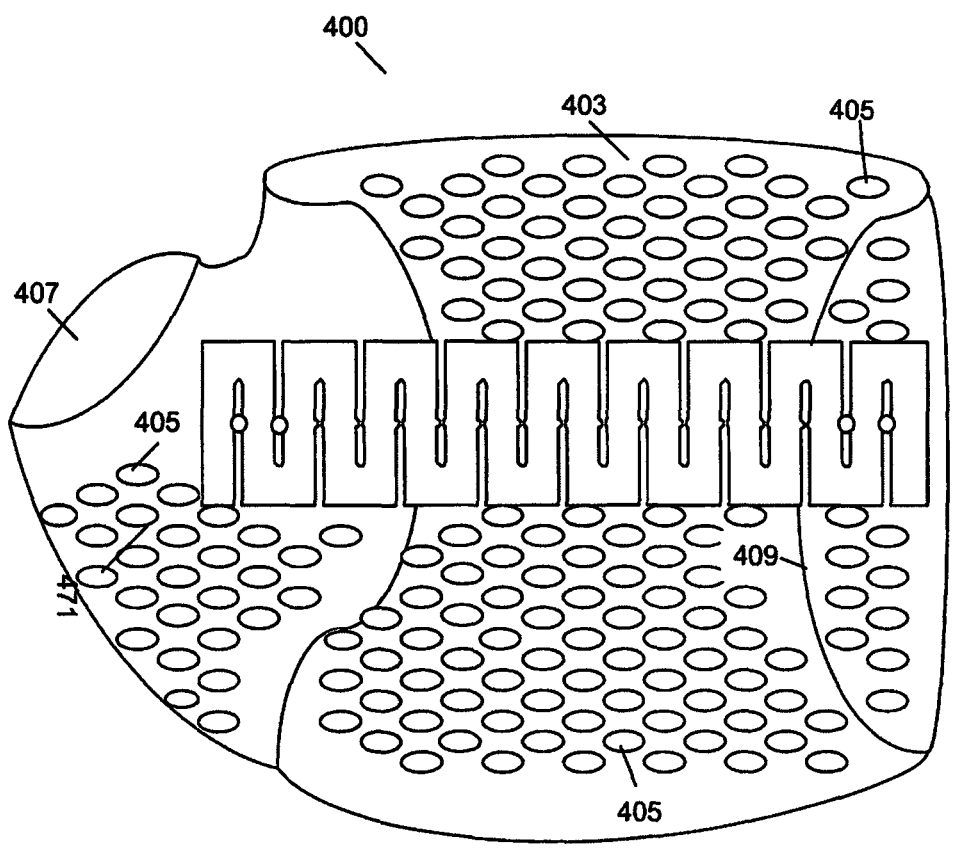
FIG. 11 illustrates a top view of an embodiment of an adjustable hand brace with an elastic adjustable member.
Figure 12:
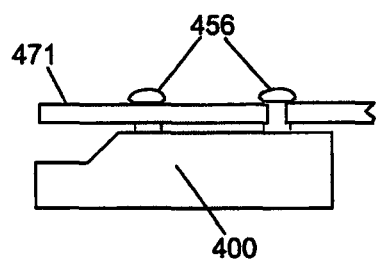
FIG. 12 illustrates a side view of a portion of an embodiment of an elastic adjustable member coupled to a brace.
Figure 13:
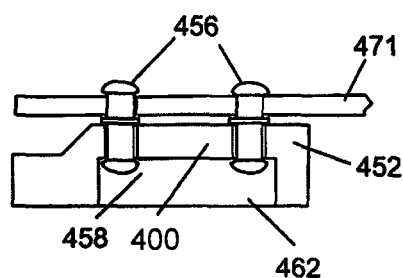
FIG. 13 illustrates a cross section side view of a portion of an embodiment of an elastic adjustable member coupled to a brace.

With reference to FIGS. 10-12, the elastic member 471 can be used on the brace 100 in place of the adjustable member 417 illustrated in FIGS. 1-3. FIG. 10 illustrates a view of the elastic member 471 on a portion 446 of the brace 400. The adjustable member 471 can be a separate component that is attached to the brace 400 but may not be an integrated part of the brace structure. With reference to FIG. 12, the elastic member 471 can be a separate structure that is attached to the brace with one or more fastening pins 456 that were described with reference to FIG. 8. This design allows the position of the elastic member 471 to be change as necessary to provide a comfortable tension and fit for the patient. The elastic member 471 may be available in different lengths or if there is excessive length, the elastic member 471 can be cut to the proper length. In an embodiment, the elastic member 471 can be stocked in various lengths and attached to the brace 100 after it has been fabricated. In an embodiment, the elastic member 471 can be created as an integrated portion of the brace 400. For example, if the brace 400 is fabricated using a 3D printing machine, the elastic member 471 can be formed with the brace 400 as a single integrated structure. FIG. 13 illustrates a cross section of a portion of the brace 400 where the elastic member 471 is coupled to the brace 400.

The illustrated braces provide the required support and protection for the patient while minimizing all unnecessary structural components. This minimalistic design matches the patient's anatomy and provides a more comfortable fit. These braces are also lighter in weight than traditional braces and provide greater ventilation. Although, the braces are shown for hands and forearms, in other embodiments, the inventive braces and automated design process can also be used for any other portion of the patient's body including elbows, feet, legs, ankles, knees, back, neck, shoulders, and other portions of the body.

In other embodiments, different width adjustable sections can be combined. For example, an adjustable brace may have thinner adjustable sections over the injured portion of the limb and wider adjustable sections at the ends of the brace. By placing thinner adjustable sections over the injury, the brace can be more accurately adjusted to properly support and protect the limb as the injured area heals.

The brace can have a smooth inner surface that corresponds closely to the patient's body and may also have an integrated construction. The brace can be designed by automated CAD workflows, such that no human operator is required. The mechanical data for a patient can be obtained from visible or infrared (IR) light photographs of the patient's body or limb. This body topography can be determined from the photographs and the topography data is then digitized and input into a CAD program that is referenced to design the cast or brace. An example of a suitable CAD program is Pro/Engineer by Parametric Technology Corporation. Other CAD software includes: SolidWorks by SolidWorks Corporation a subsidiary of Dassault Systèmes, S. A.

For simplicity, the inventive custom brace will be described as a conformal hand brace, however the same processes can be used to form an arm or back brace or any other body brace, cast or device. The brace can be a hard and strong structure that is designed to surround and support the injured portion of the body or limb.

In a preferred embodiment, a photogrammetry, depth mapping or image correlation technique or other type of photographic surface detection method is used to obtain the outer surface measurements which can be a set of 3-dimensional coordinates that define the outer surface of the patient's leg or any other body part. Photogrammetry in its broadest sense reverses the photographic process by converting flat 2-dimensional images of objects back into the real 3-dimensional object surface. Two or more different photographs can be required to reconstruct a 3-dimensional object. In a perfect photogrammetry process, two photographs would provide enough information to perfectly reconstruct the 3-dimensional object. Unfortunately, the photography and measuring process are generally not perfect so the reconstruction of the 3-dimensional object based upon two photos will also have defects. The photogrammetry object measurement process can be improved by taking more photographs and using the extra information to improve the accuracy. The photogrammetry process will produce a set of 3-dimensional coordinates representing a surface of an object from the measurements obtained from the multiple photographs.

Photogrammetry uses the principle of triangulation, whereby intersecting lines in space are used to compute the location of a point in all three, XYZ dimensions. In an embodiment, multiple cameras are used to photograph the leg or body part simultaneously. In other embodiments, a light from a light source that is a known distance from a camera is projected onto a patient and a photograph of the patient is taken. By triangulating each of the points of light, the distances from the camera to each point of light can be determined. In order to triangulate a set of points one must also know the camera positions and aiming angles also called the "orientation" for all the pictures in the set. A process called resection is used to determine the camera positions and aiming angle calculations for each camera. The cameras should also be calibrated so their errors can be defined and removed.

Triangulation is the principle used by photogrammetry to produce 3-dimensional point measurements. By mathematically intersecting converging lines in space, the precise locations of the points can be determined. Photogrammetry can simultaneously measure multiple points with virtually no limit on the number of simultaneously triangulated points. By taking pictures from at least two or more different locations and measuring the same target in each picture a "line of sight" is developed from each camera location to the target. Since the camera locations and aiming directions are known, the lines can be mathematically intersected to produce the XYZ coordinates of each targeted point. When a pattern of IR or visible light points are projected onto the patient, triangulation can also be used to determine the locations of these points based upon the distance between the light source and the camera and the detected angles of the points.

Resection is the procedure used to determine the coordinates of the object from photograph data, based upon the camera positions and aiming directions, also known as the orientation of the camera. Typically, all the points that are seen and known in XYZ coordinates in the image are used to determine this orientation. For an accurate resection, you may have at twelve or more well-distributed points in each photograph. If the XYZ coordinates of the points on the object are known, the camera's orientation can be computed. It is important to realize that both the position and aiming direction of the camera are needed for resection. It is not sufficient to know only the camera's position since the camera could be located in the same place but be aimed in any direction. Consequently, the camera's position which is defined by three coordinates, and where it is aimed which is defined by three angular coordinates must be known. Thus, although three values are needed to define the X, Y and Z coordinates of a target point, six values may be required to define a point on a picture, XYZ coordinates for position, and XYZ angles for the aiming direction.

The surface being photographed should also have a minimum number of well-distributed reference points that appear on each photograph and for an accurate surface measurement. The reference points can be visible marks placed on the object that provide a visible contrast that will be clearly shown on the photographs. There should be at least twelve well-distributed reference points on each photograph and at least twenty points for the entire surface of the object. The reference points should be evenly distributed on the object and throughout the photograph. The surface of the object can be more accurately measured with a larger number of reference points.

In an embodiment, the patient's natural features including: freckles, spots, wrinkles, pores and other features can be used as the reference points. Alternatively, IR or visible light can be projected onto the patient to provide the reference points for photographic measurement. It is also possible to mark the patient's skin with ink markers and in an embodiment, the patient or patient's limb can be covered with a form fitting material such as an elastic cotton tube, stockinette, leotard, body suit.

In an embodiment, a computer program processes the photographic measurements to produce the final XYZ coordinates of all the measured points. In order to do this, the program triangulates the target points and resects the pictures. The program may also calibrate the camera. Typical accuracies of the three dimensional measurements can be very high under ideal operating conditions. For example, the measurements can be accurate to 50-100 microns (0.002" to 0.004"). However, the accuracy of a photogrammetric measurement can vary significantly since accuracy depends on several inter-related factors. Important accuracy factors include: the resolution and quality of the camera, the size of the object being measured, the number of photographs taken, and the geometric layout of the pictures relative to the object and to each other.

Photogrammetric measurements can be dimensionless. To scale a photogrammetric measurement, at least one known distance is required. The known distance can be a distance marked on the object, a known distance between cameras or a known distance between a light source and a camera. For example, if the actual coordinates for some targeted points are known, the distances between these points can be determined and the points can be used to scale the measurement. Another possibility is to use a fixture with targets on it and measure the fixture along with the object. Because the distance between the targets on the fixture is known, it can be used to scale the other measurements between reference points on the object. Such fixtures are commonly called scale bars. The patient topography dimensions can also be determined by knowing a distance between two cameras and the angles of lines between the cameras and the points on the patient. From this information, the distances between the cameras and the points on the patient can be determined by triangulation. Similarly, the patient topography dimensions can also be determined by knowing a distance between a light beam source and a camera, an angle of the light beams from a source and the angles of the light points detected by the camera. From this information, the distances between the camera and the light points on the patient can be determined by triangulation. The light can be infrared and the camera can be an infrared camera that produces infrared photographs.

In order to define common surface points on the hand, reference points can be placed on the hand. The reference points can simply be any contrasting color points, patterns, shapes, objects, symbols or other optical indicators which are easily visible. The reference points can be black or colored ink marks that are placed on the body with a pen. In other embodiments, the reference points can be lights such as visible light, infrared light, points or grids, stickers or objects or any other visible point of reference. For example, circular adhesive stickers which have a contrasting color can be placed on the patient and photographed. The stickers can provide accurate reference points which can be used to produce the digital representation of the patient's limb and/or body. In the preferred embodiment, the reference points are placed and evenly distributed around the entire limb or portion of the body that the brace is being constructed for.

Figure 14:
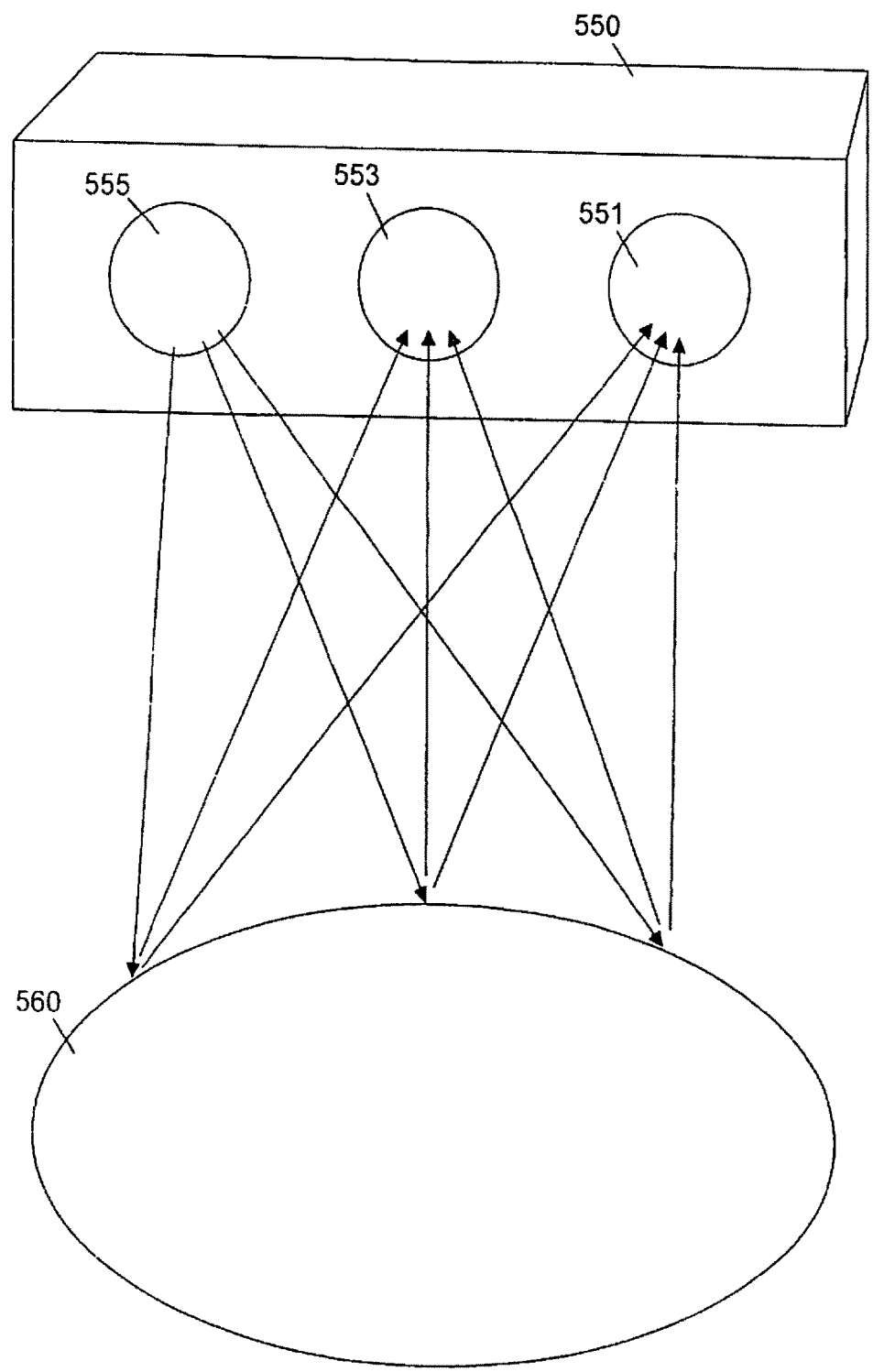
FIGS. 14-17 illustrates an IR and visible light photographic system for detecting a surface of a patient.

With reference to FIG. 14, in an embodiment the three dimensional surface data of a patient can be obtained using an optical device comprising a color image camera 551, an infrared (IR) camera 553 and an infrared (IR) light source 555 coupled to a signal processor. The IR light source 555, IR camera 553 and color image camera 551 can all be mounted on one side of the optical device 550 so that the color camera 551 and IR camera 553 have substantially the same field of view and the IR light source 551 projects light within this same field of view. The IR light source 555, IR camera 553 and color image camera 551 can be mounted at fixed and known distances from each other on the optical device 550. The color image camera 551 can provide color information for the patient's limb 560 or portion of the patient within the viewing region of the camera 551. The IR camera 553 and IR light source 555 can provide distance information for each area of the patient's limb 560 exposed to the IR light source 555 that is within the viewing region of the IR camera 553. The infrared light source 555 can include an infrared laser diode and a diffuser. The laser diode can direct an infrared light beam at the diffuser causing a pseudo random speckle or structured light pattern to be projected onto the patient's limb 560. The diffuser can be a diffraction grating which can be a computer-generated hologram (CGH) with a specific periodic structure. The IR camera 553 sensor can be a CMOS detector with a band-pass filter centered at the IR laser wavelength. In an embodiment, the color image camera 551 can also detect the IR light projected onto the patient's limb 560.

Figure 15:
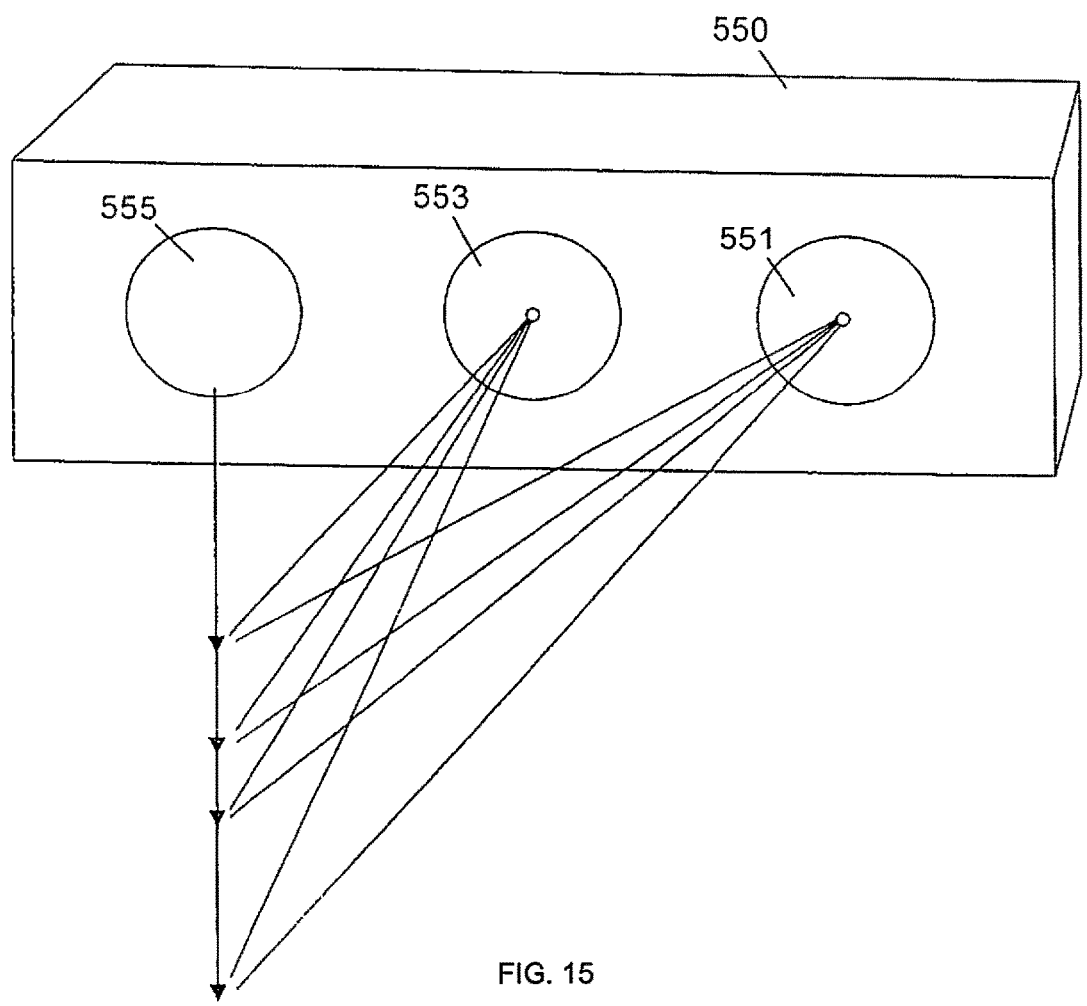

With reference to FIG. 15, the optical device 550 can detect the distance between the infrared camera 553 and the IR light on the patient because the camera 553 sees the patient's limb at a different angle than the infrared light source 555 and the distance between infrared light source 555 and IR camera 553 is defined. The principle of structured light distance sensing is that given a specific angle between IR light source 555 and IR sensor 553 for each point of light on the patient's limb and a distance between the object and the IR light source 555 or IR camera 553 or color camera 551 can be determined by triangulation. The angles of the light points on the patient's limb detected by the IR camera 553 and the color camera 551 will change depending upon the distance of the patient from the optical device 550. In an embodiment, a calibration process can be used to determine the angles of each light point on a plane at different distances from the optical device 550. By knowing the angles and corresponding distances for each point of IR light and distance of the points of light from the optical device 550 can be determined. These distance calculations for an object can also be known as three dimensional mapping. The distance value for each light point can also be matched with the visible color image data so that color and distance information for each pixel of a patient image can be determined and stored.

Because a single picture can capture the patient in a fixed position, the IR light source 555 can be project the IR light on the patient and the IR camera 553 can take a single photograph of the patient 560. The color camera 551 may also simultaneously take a single photograph of the patient's limb 560. In other embodiments, multiple IR or color photographic images can be taken of the patient's limb 560 in different positions and the corresponding image shifts are directly relates to distance from the camera. Each successive photographic image is served as a reference photograph for the next frame calculation so that the movement of the patient can be detected and the changes in the three dimensional mapping can be recorded.

Figure 16:
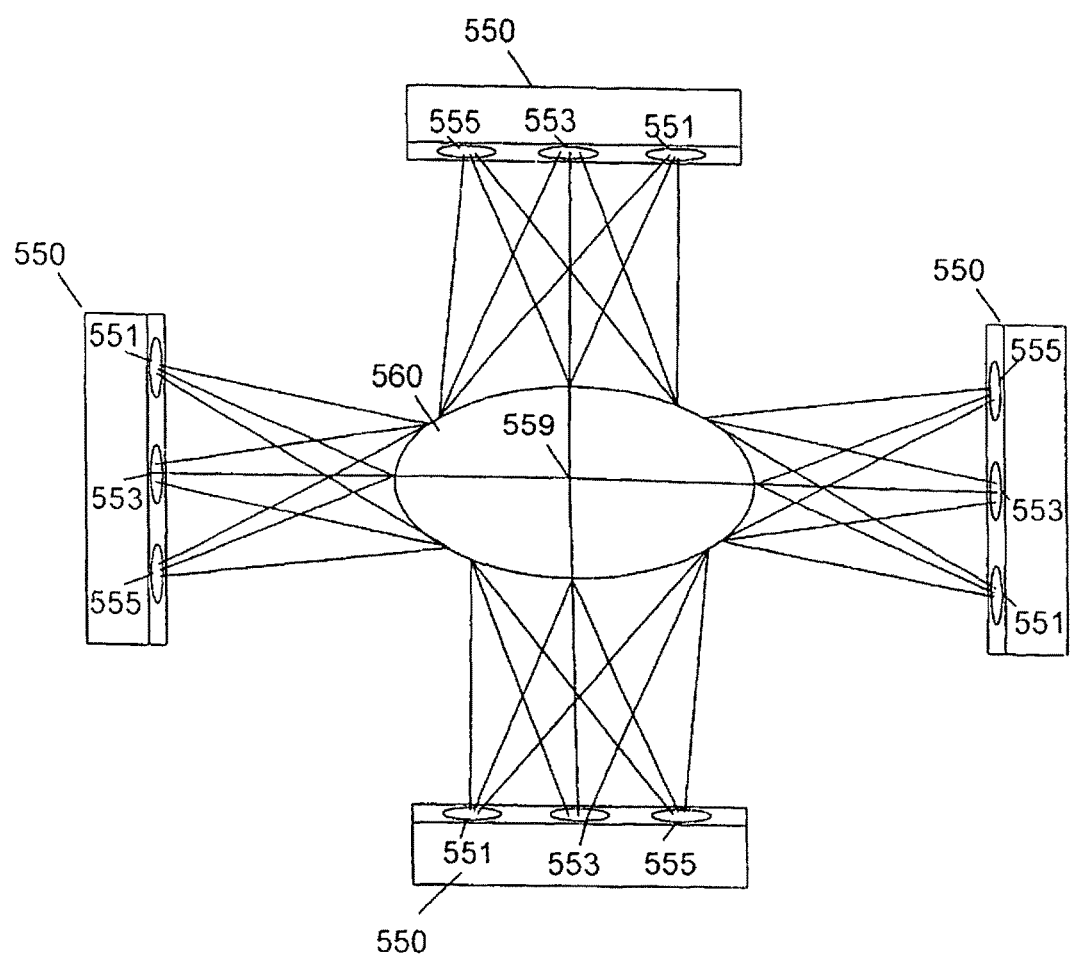

As discussed, the IR camera can detect the light pattern projected onto the patient's limb and through triangulation, the distance between the IR camera and color camera and each point of the light pattern on the patient can be determined. However, the distance information for the points can only determine a three dimensional surface of the patient's limb or a portion of the patient's limb that are detected by the IR camera 553 or the color camera 551. With reference to FIG. 16, in order to determine a three dimensional surface around a patient's limb, multiple optical devices 550 can be placed around the patient and the three dimensional surface information from each of these cameras can be combined to determine the three dimensional surfaces around a circumference of a patient's limb. In an embodiment the IR light from each of the IR light sources 555 can be emitted simultaneously and the photographs from all of the IR cameras 553 and color cameras 551 can be taken simultaneously. In other embodiments, the IR light sources 555 can interfere with the IR cameras 553 that are not part of the same optical system 550. Rather than protecting IR light from all of the IR light sources 555 at the same time, the optical systems 550 can be configured to sequentially illuminate with IR light and photograph the patient's limb 560. A first optical system 550 will emit the IR light and take IR and color photos of the patient's limb 560. The first optical system 550 can then stop projecting IR light onto the patient's limb 560 and the second optical system 550 can then emit the IR light, take IR and color photos of the patient's limb 560. The second optical system 550 can then stop projecting IR light onto the patient's limb 560. This described process can be sequentially repeated for the remaining optical systems 550.

After taking the IR photographs, surface data for different sides of the patient's limb 560 can be combined from the optical systems 550 in various different ways. For example, the multiple IR cameras 553 can produce distance information for the photographed patient's limb 560 that can be combined using a photogrammetry process to determine a full or partial circumferential three dimensional representation of the patient's limb 560. The surface data from the optical systems 550 will include some of the same surface areas of the patient's limb 560 that were also captured by at least two of the adjacent optical system 550. Because the three dimensional shape data is the same, the system can identify these matching surface shapes and combine the surface data to obtain continuous surface data for the photographed portion of the patient's limb 560. In an embodiment, the optical systems 550 can be aligned around the patient 560 with the IR cameras 553 radially aligned in a planar manner and directed towards a center point 559 within a cross section of the patient's limb 560. The optical systems 550 can each produce surface data for a portion of the patient's limb 560. Because the IR photos are taken on a common plane, the surface data from the different optical systems 550 can be joined by determining the distance of the surface data from the center point 559. In an embodiment, a first set of calibration IR and/or color photographs can be taken by the optical systems 550 of a physical center point marker 559 without the patient's limb 560. IR and/or color photos can then be taken of the patient 560. From this information, the position of the center point 559 relative to the surface data of the patient 560 can be determined. By knowing the distances and alignment of the surface data to a common center point 559, the surface data from the different optical systems 550 can be combined. In an embodiment, the optical systems 550 can be arranged on direct opposite sides of the patient's limb 560. Although four optical systems 550 are shown, in other embodiments, two or more optical systems 550 can be used to obtain the surface data for the patient's limb 560. Three optical systems 550 may be required to have some overlapping surface data for the patient's limb 560.

Figure 17:
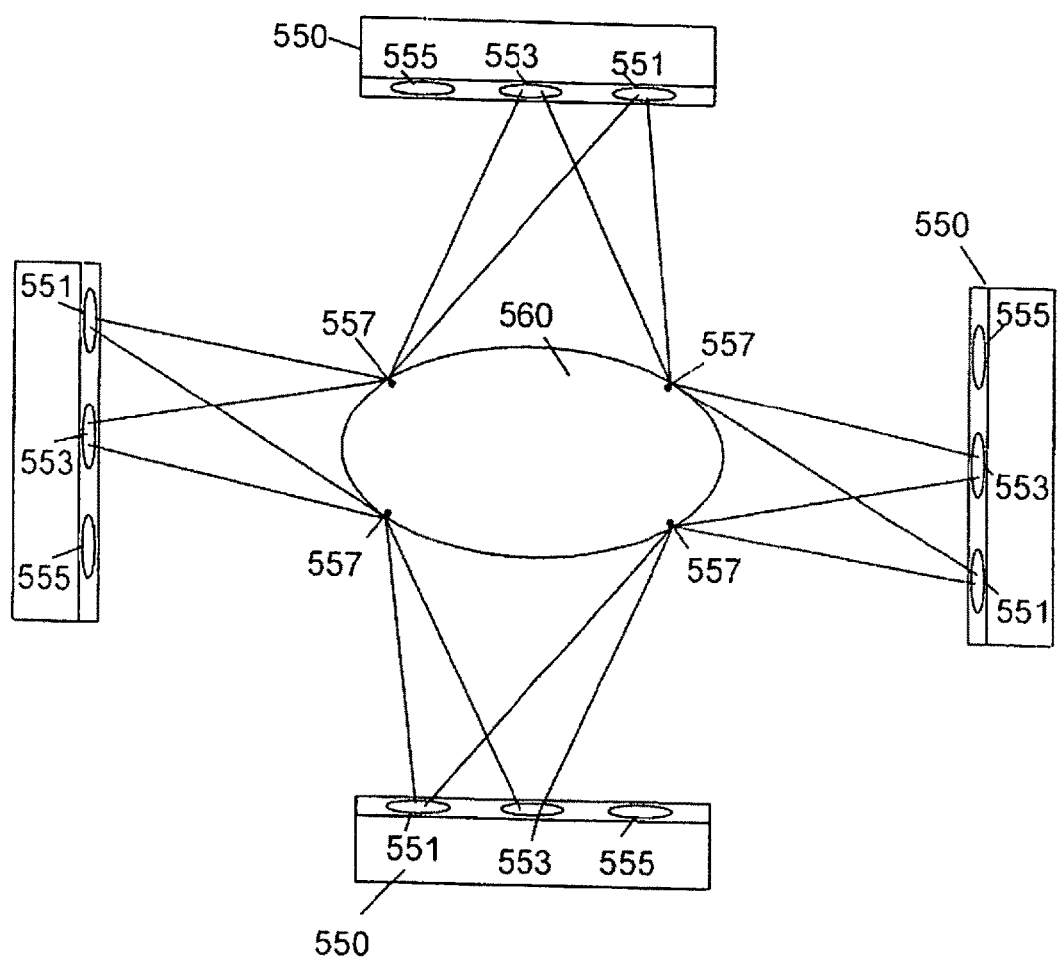

With reference to FIG. 17, in other embodiments the surface data from the optical systems 550 can be combined by using alignment markings 557 on the patient's hand or limb 560. The patient's limb 560 may be covered with a material and a visible or IR marking 557 can be projected onto the patient's hand or limb 560 at locations that are within the field of view of two or more optical systems 550. The color camera 551 may detect both visible and IR markings and the IR camera 553 may only detect IR markings. The optical systems can be able to distinguish the IR light from the IR markings because the shape of the IR marking 557 can be larger or may have a different shape. The surface data from adjacent optical systems 550 can be combined by using a photogrammetry or image correlation process that matches the positions of the markings 557 that are photographed by both optical systems 550.

Automatic Brace Design

In an embodiment, the inventive hand brace can be designed automatically based upon a plurality of reference measurements of the patient's hand. With reference to FIGS. 18 and 19, a hand and specific anatomical structures are illustrated. FIG. 18 illustrates a palmar side of the hand and FIG. 19 illustrates a dorsal side of the hand 135. The anatomical structures include: the proximal phalanx segments 221 of the fingers, the palmar digital creases 231, the distal palmar crease 223, the proximal palmar crease 225, the thenar crease 227 and the wrist crease 229. Because the fingers bend towards the palmar side of the hand 135, these creases may only be visible on the palmar side of the hand 135. The hand 135 may also include anatomical points that can be marked with stickers or any other type of markings that can improve the accuracy of the measurements for these points. These marked anatomical points can include: finger metacarpophalangeal (MCP) joints 224, the thumb MCP joint 226, radial styloid 228, and the ulnar styloid 230. The MCP joint and styloid points may be marked on either side of the hand. In an embodiment, the MCP joint and styloid points can be marked on one side of the hand 135 and the system can identify these points and points for these anatomical features on the opposite side of the hand. For example, if the MCP joint and styloid points are identified on the surface of the dorsal side, the system can process this information and also identify the locations of the MCP joint and styloid points on the surface of the opposite palmar side of the hand 135. The system can also function in the reverse manner with the system identifying points marked on the dorsal side of the hand based upon markings on the palmar side of the hand In an embodiment, the system can use the location information to design a portion or the entire the brace. The system can design the brace either with additional input from a brace designer or fully automatically.

By identifying and referencing these visible anatomical features of the hand during the design process, the hand brace can be designed to cover specific areas of the hand to prevent specific types of movement or avoid certain areas of the hand to allow movement of specific joints or parts of the hand or limb. In an embodiment, the photographic process used to create a digital representation of the body may be able to identify these features and provide graphical identifications of these features on a display coupled to a design computer. The brace can then be designed to restrict or accommodate movement of specific areas of the hand.

Several points on the hand are marked with "+" within circle symbols. These markings indicate the locations of the small finger MCP joint 224, the ring finger MCP joint 224, the middle finger MCP joint 224, the index finger MCP joint 224, thumb MCP joint 226, the radial styloid 228, and the ulnar styloid 230. The circled numbers in the photograph illustrate various design points and dimensions for the brace. Various portions of the brace design will be described with reference to the measured anatomical points and the circled numbers on the drawings. In an embodiment, the surface topography data and the marked anatomical feature positions can provide enough information for a computer to automatically design a brace for the limb. The measurements of the hand can be used to automatically design the hand brace with specific geometric relationships between the hand measurements and the brace design. The following descriptions provide examples of possible methods for fully specifying the design of a hand brace such that a computer can automatically generate the brace.

Figure 20:
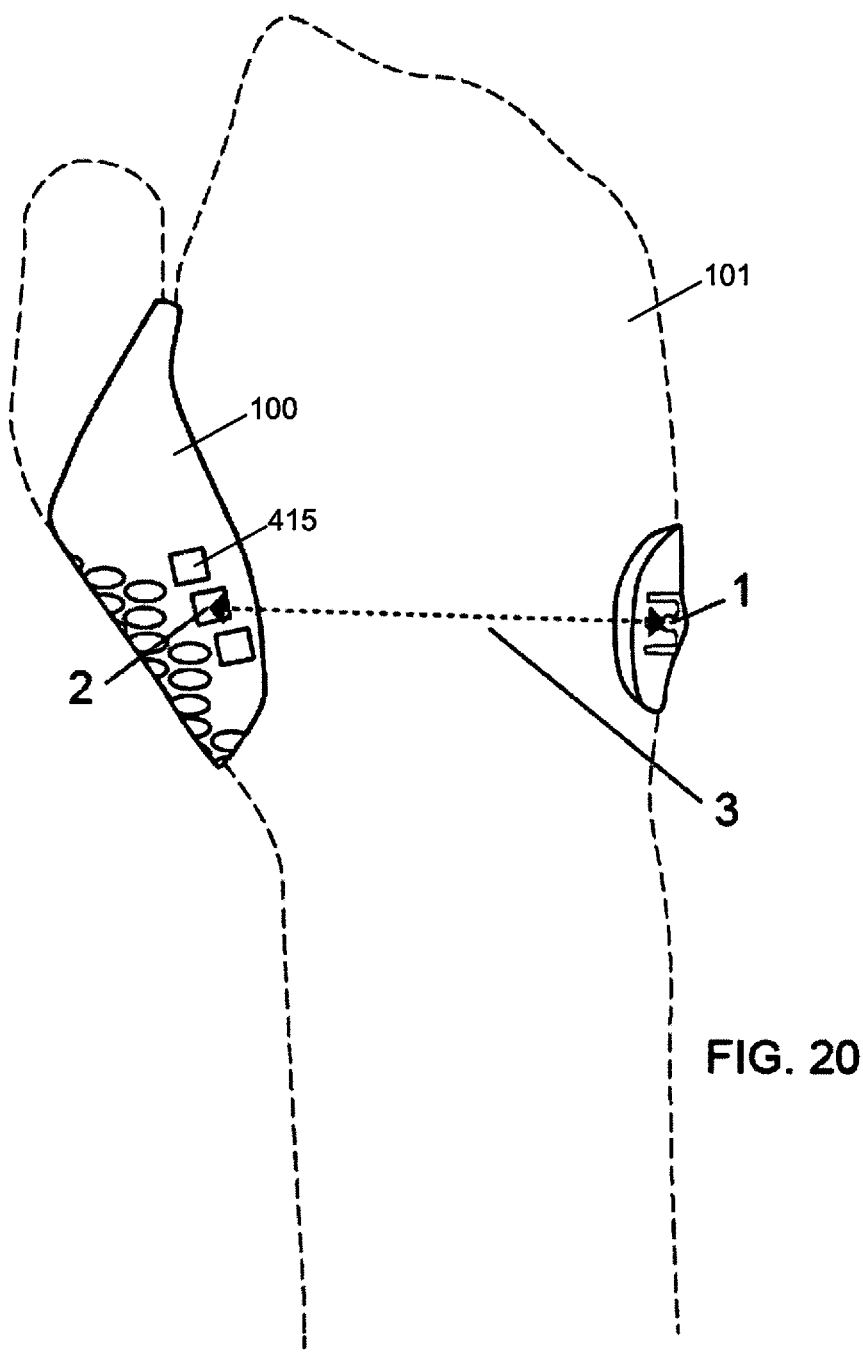
FIG. 20 illustrates a top view of a hand with hand brace design features.

With reference to FIG. 20, a wrist brace design 100 is illustrated on a hand 101. Point 1 can be the start location for the band at the middle of the brace on the small finger side on the back of the hand 101. Point 2 can be on the thumb side of the back of the hand 101 and may be 4-5 mm beyond the center point of the center asset 3. The center asset 3 can be the center line of the brace 100 but it can also be a line that is at an oblique angle to the brace 100. The center asset 3 can be the arc length of the band or strap that extends over the back of the hand 101. The arc length is determined by the geometry from the scan of the patient's hand 101. The curve of the arc originates from the start point 1 and the end point is along the mesh on the thumb side of the back of the hand 101. The center asset 3 can represent the line of the band which can have a beginning point that can be over the extent on the small finger side and the end point of the line can be the center of the negative latching object.

Removable Band

Figure 21:
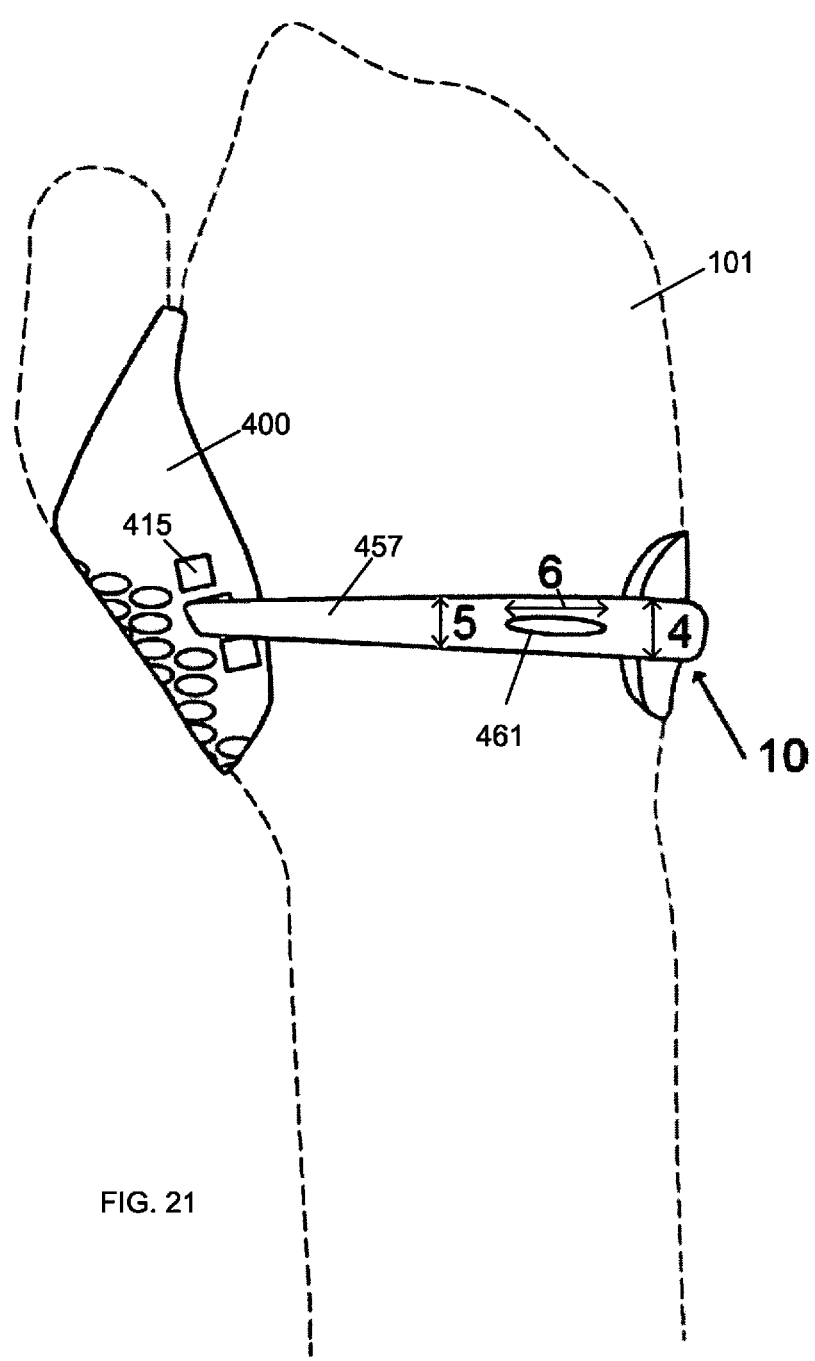
FIG. 21 illustrates a top view of a hand with a hand brace and adjustable member design features.

In an embodiment the band 457 may be removable rather than being integrated with the wrist brace 100. With reference to FIG. 21, a brace 100 with a removable band 457 on a hand 101 is illustrated. The line of the band 457 can have a beginning point that is approximately at the center of the extent on the small finger side and have an ending point at the center of the negative latching object. The removable band 457 can include couplings at the proximal and distal portions. The proximal portion of the removable band 457 can be coupled to the brace 100 at a location that can be aligned approximately with the middle of the small finger on the back of the hand 101 plus about 3 mm to 9 mm. The end location of the band 457 can extend around the back of the hand 101 about 3 mm to 7 mm beyond the center point of the asset. The arc length of the band can be determined by the curvature geometry from the patient's hand 101. The dimension 4 is the width of the band 457 at the start area at the small finger side. The width dimension 4 can be between about 8-14 mm. The dimension 5 is the width of the band 457 in the middle section of the removable band 457 which can be about 4-11 mm wide or about 50% to 70% of the width at the proximal end of the removable band 457. The width at the distal end of the band 457 can be about 3 mm to 8 mm wide. In an embodiment, the band 457 can have a continuous taper along the entire length, an asymmetric taper or a constant width and no taper at all. The length of the taper of the band 457 from the proximal end along the length of the band 457 can be about twice the length of the hole in the band 457. A radius at the base 10 of the band 457 can be about 0.5-2 mm.

The illustrated embodiment of the band 457 includes an elliptical hole 461. The elliptical hole 461 can be located at the edge of the brace by point 1 at the middle of the band 457 on the small finger side on the back or dorsal side of the hand 101. The dimension 6 is the length of an elliptical hole 461 which can be about 10-18 mm long and the hole 461 can be about 1-4 mm wide or about 110% to 150% of the length of the width of the band 457 at the proximal end. The width of the hole 461 can be about 2.0-3.0 mm.

Figure 22:
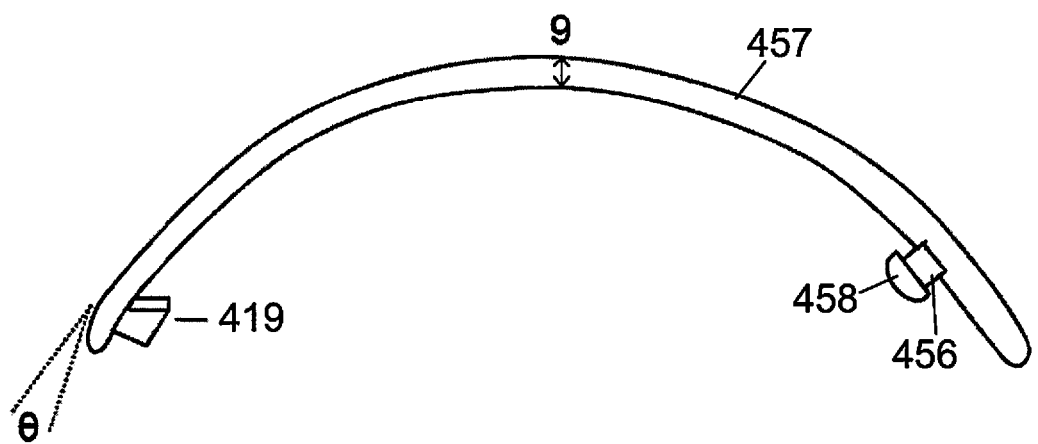
FIG. 22 illustrates a side view of an embodiment of an adjustable member.

With reference to FIG. 22, a side view of the band 457 is illustrated. The thickness 9 of the band 457 can be between about 1 mm and 3 mm. The distal end of the band can be rotated downward at the tip towards the surface of the hand to prevent the hook 419 from catching on other objects. In an embodiment, the tip of the band 457 can be angled downward at an angle Θ between about 5 to 15 degrees. In an embodiment, the band 457 can twist along the length of the band 457. This twisting can correspond to the relative orientation of the start and end locations of the brace on the arm. In an embodiment, the band includes a "kink" over the portion of the band that is over the second metacarpal. The kink shape allows the band to avoid contact with the patient over the second metacarpal.

As discussed above with reference to FIG. 1, the band 457 can be secured around the hand to hold the brace on the hand. A hook 419 at the distal end of the band 457 can be manually pulled to the desired tension. The brace 100 can have a plurality of holes and the hook 419 can be placed into the hole 415 that provides the desired tension. The plurality of fastener holes 415 can each provide a different distance so that placing the hook 419 of the band 457 in different holes 415 can allow the user to alter the circumference of the brace. In FIG. 20, the holes 415 towards the finger end of the brace are further in distance from the point 1. Thus, placing the hook 457 in the hole 415 closer to the fingers will produce a tighter fit and placing the hook 457 in a hole 415 towards the wrist will produce a looser fit. In other embodiments, the holes 415 can be arranged in any other configuration that provides multiple adjustable member settings.

Back of Hand Small Finger Side

Figure 23:
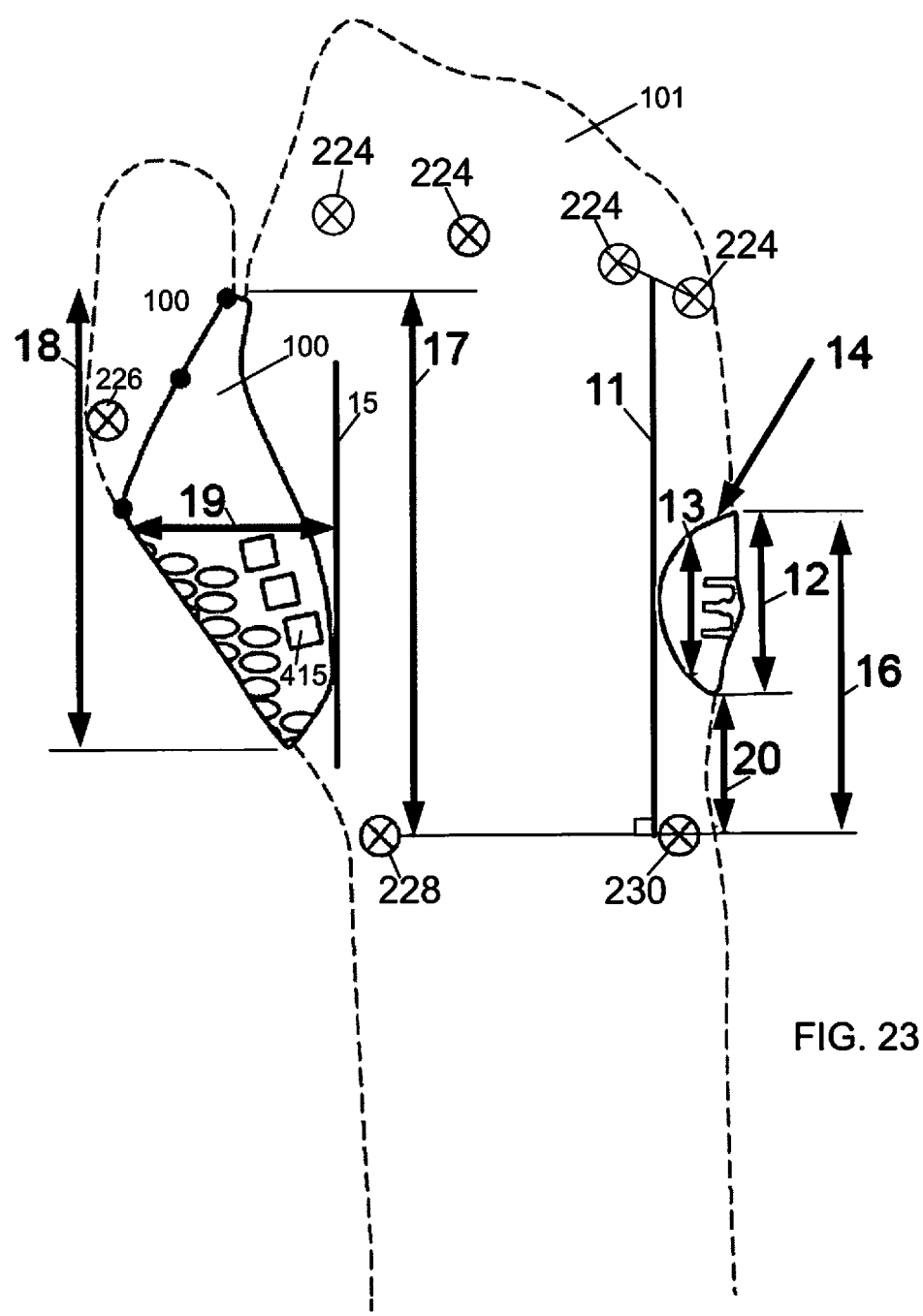
FIG. 23 illustrates top views of a hand with hand brace design features.

With reference to FIG. 23, a back portion of the hand 101 wearing a wrist brace 100 is illustrated. The line 11 is the extent defined by a line that is drawn perpendicular to the line connecting the ulnar styloid 230 and radial styloid 228 to midpoint of the line connecting the small finger MCP joint 224 and ring MCP joint 224. The length 12 is the width of the brace 100 at the small finger side in the coronal plane. The length 12 of the brace 100 on the line connecting the small finger MCP joint 224 and the ulnar styloid 230 in the coronal plane can be about 30% to 50% of the distance measured in the coronal plane between the small finger MCP joint 224 and ulnar styloid 230. The proximal extent 20 of the brace 100 wraps around the hand 101 and is measured in the coronal plane which can be about 15% to 35% of the distance between the small finger MCP joint 224 and ulnar styloid 230. The width of the brace 100 at the extent 13 located where the extent of the back of the hand 101 is defined and can be about 50%-70% of the width 12 of the brace 100 at the small finger side. The start of the arc segment 14 adjacent to the proximal end of the strap can be about 40%-60% of the way from the side of the hand 101 at the coronal plane to the extent. The radius of the arc segment 14 can be about 20%-30% of the width at the small finger in the coronal plane. The distal extent in the coronal plane 16 can be the distance from the ulnar styloid 230 to the distal extent in the coronal plane which can be about 60% to 80% of the distance between the small finger MCP joint 224 and the ulnar styloid 230. The distance 20 can be the distal extent 16 minus the width 12 of the brace 100 at the small finger side.

Back of Hand Thumb Side

With reference to FIG. 23, the distal extent is the distance 17 from the radial styloid 228 to the distal extent in the coronal plane which can be approximately equal to the distance between the middle finger MCP joint 222 and the radial styloid 228. The width of the thumb region 18 of the brace 100 in the coronal plane can be about 45% to 65% of the distance measured in the coronal plane from the radial styloid 228 to the middle finger MCP joint 222. The extent onto the back of the hand 101 can be a line 15 that is perpendicular to the line connecting the radial styloid 228 and ulnar styloid 230 up to the top center of the index finger MCP joint 224. The brace 100 can extend around the lateral back side of the hand 101 up to the line 15 as represented by line 19.

Figure 24:
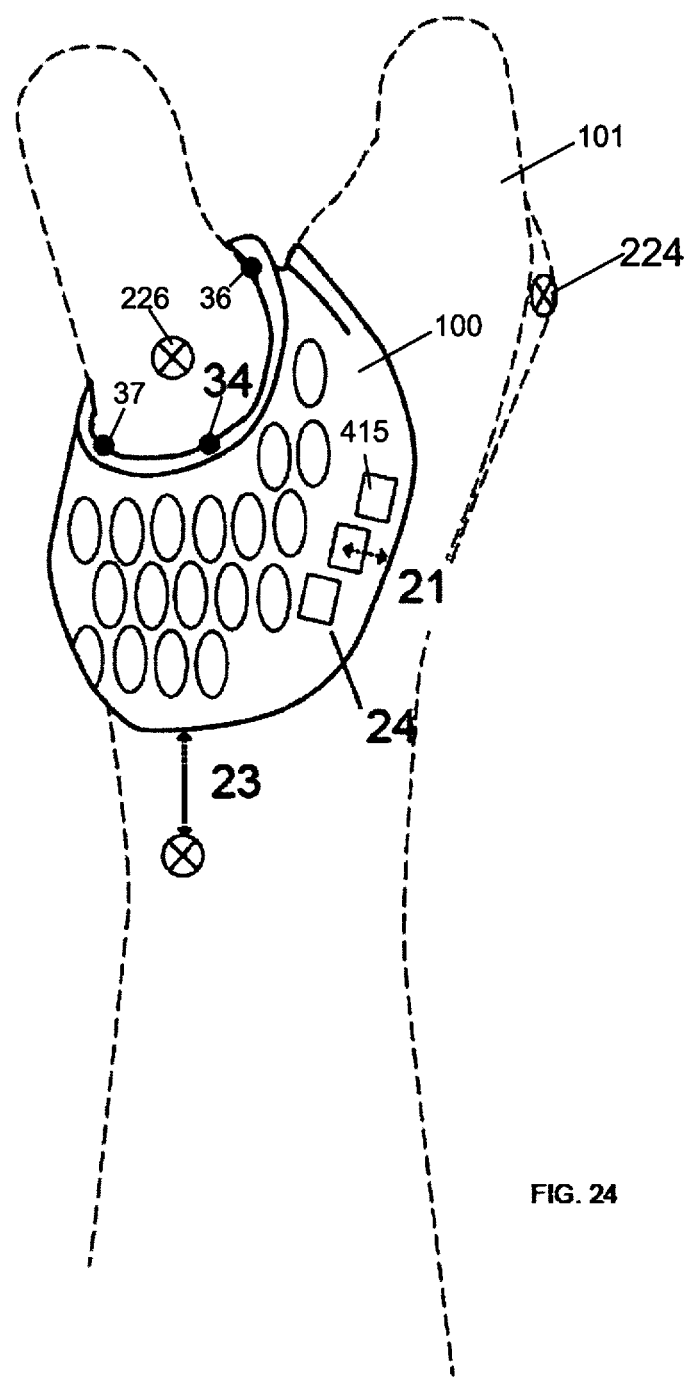
FIG. 24 illustrates a side view of a hand with hand brace design features.

With reference to FIG. 24, a side view of the thumb side of the brace 100 is illustrated. The distance 21 from the lateral edge of the brace 100 to the center of the asset 415 can be about 5-30 mm from the lateral edge of the brace 100 to the center of the asset 415. The positions of the assets 415 can be about 40%-60% of the length on the radial/index line 17 from the radial styloid 228 to the distal edge of the brace 100. The point of taper of the brace 100 can begin once the brace 100 has crossed the line connecting the point on the side of the index MCP joint 224 to the radial styloid 228. The proximal extent across the side of the hand 101 can be the distance 23 from radial styloid 228 to proximal extent of the brace 100 where it crosses around the side of the hand 101.

Figure 26:
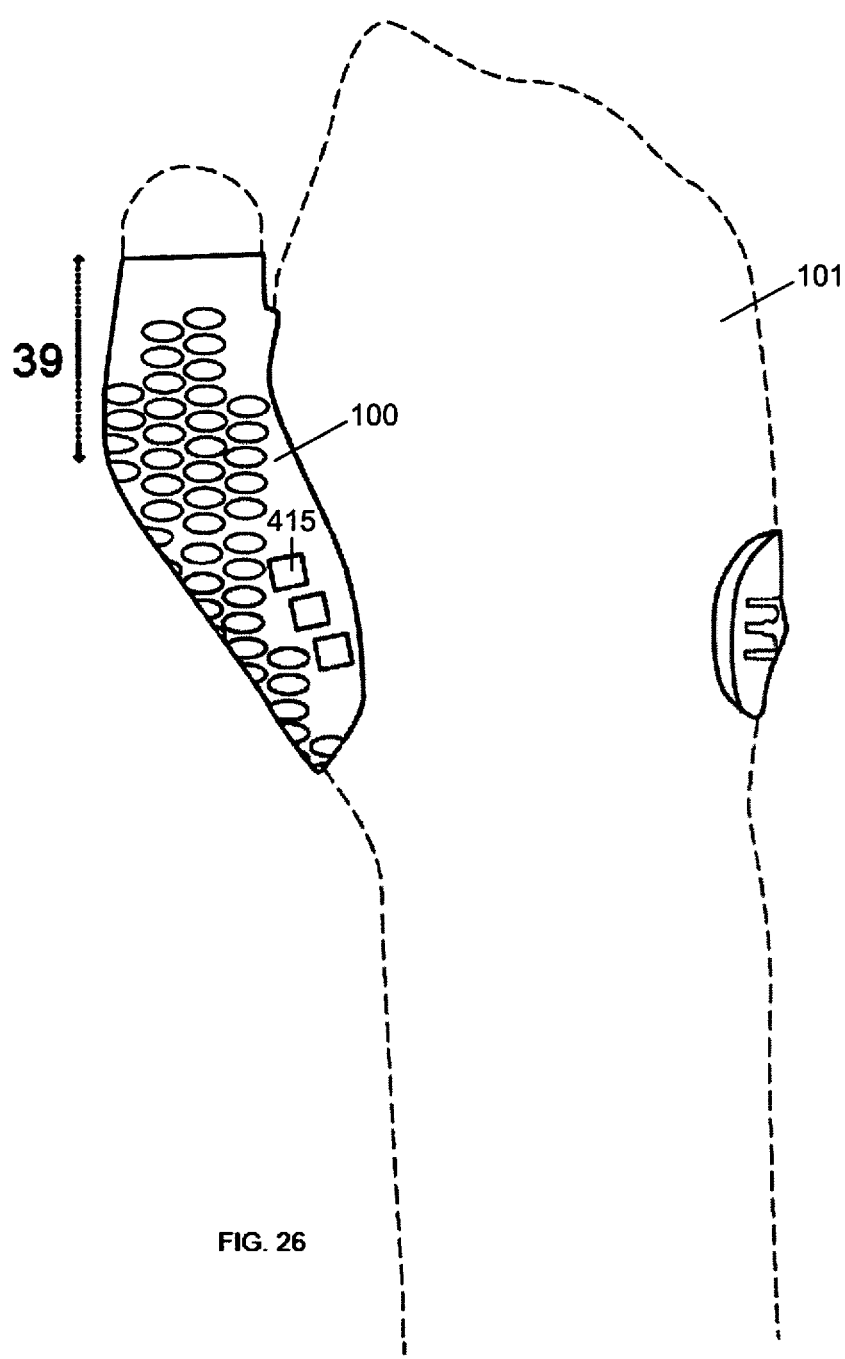
FIG. 26 illustrates a top view of a hand with hand brace design features.
Figure 27:
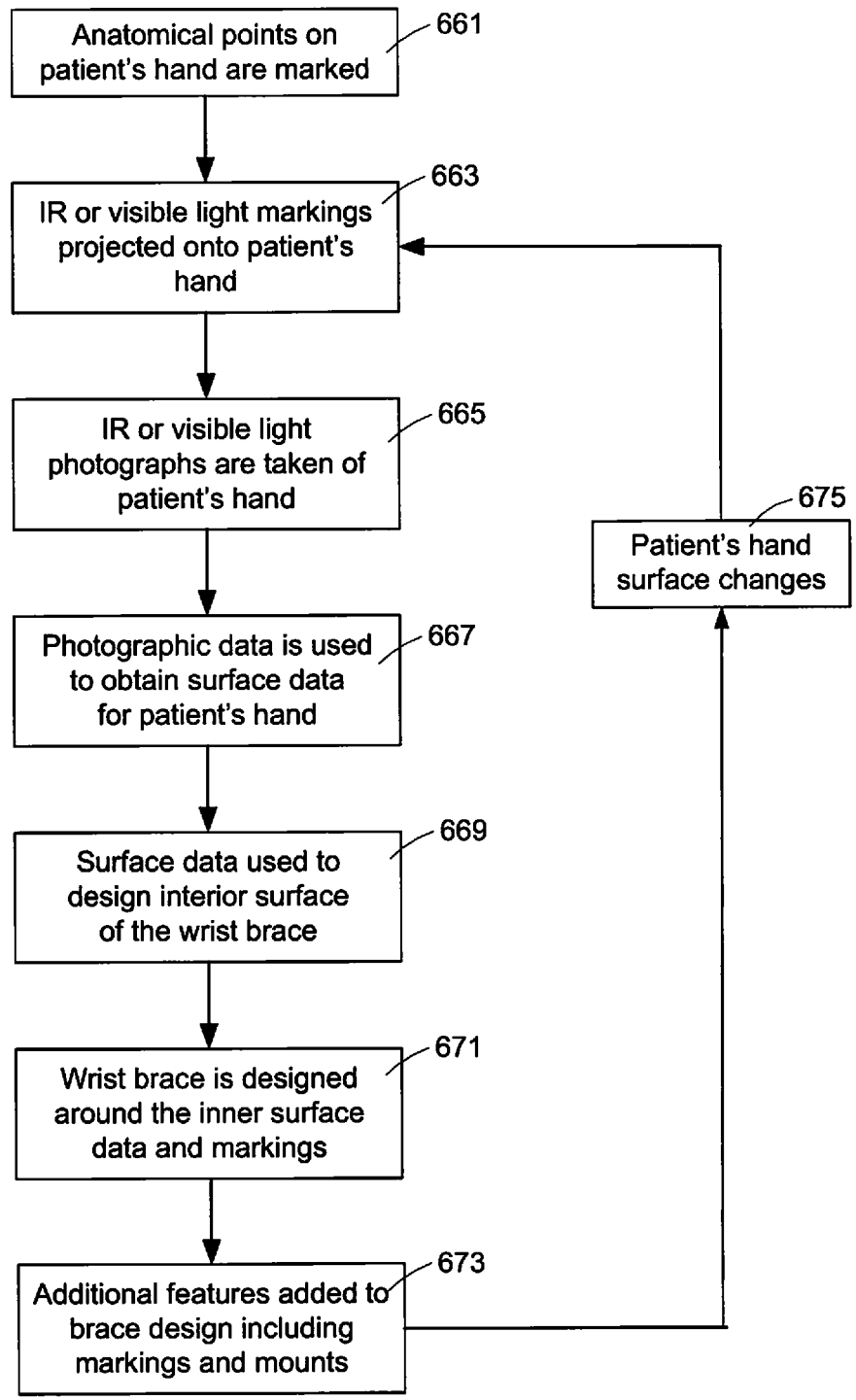
FIG. 27 illustrates an automated hand brace flow chart.

The hand brace can have various thumb sections. For simplicity, the thumb sections are described in this application as low thumb or high thumb hand brace designs. However, in other embodiments, the thumb portion of the hand brace can extend any distance up and around the thumb. With reference to FIG. 26, the thumb height dorsal 39 can be the distance from thumb MCP joint sticker 226 which can be about 15-25 mm or 20 mm above the thumb marker for high version for high thumb version and about 5-15 mm above or 10 mm below thumb marker for low version. The thumb height dimension 39 can be the distance from the thumb MCP joint 226 to proximal edge of brace which can depend upon the size of the hand. In an embodiment, the thumb height can be scaled based upon the size of the hand.

Low Thumb

The low thumb hand brace design illustrated in FIG. 24 only surrounds the lower portion of the thumb. The low thumb portion of the brace 100 can be defined by four points on the distal edge of the thumb portion of the brace 100. The low thumb length can be measured along the line between the radial styloid 228 to the thumb MCP joint point 226. In an embodiment, the low thumb length can be on a portion of a line from the thumb MCP joint sticker 226 proximally towards the radial styloid 228 to the distal edge of the brace 100. This distance from the thumb MCP joint 226 to point 34 on the edge of the thumb portion of the brace 100 can be about 15%-21% of the distance between the thumb MCP joint 226 to the radial styloid marking 228.

Figure 25:
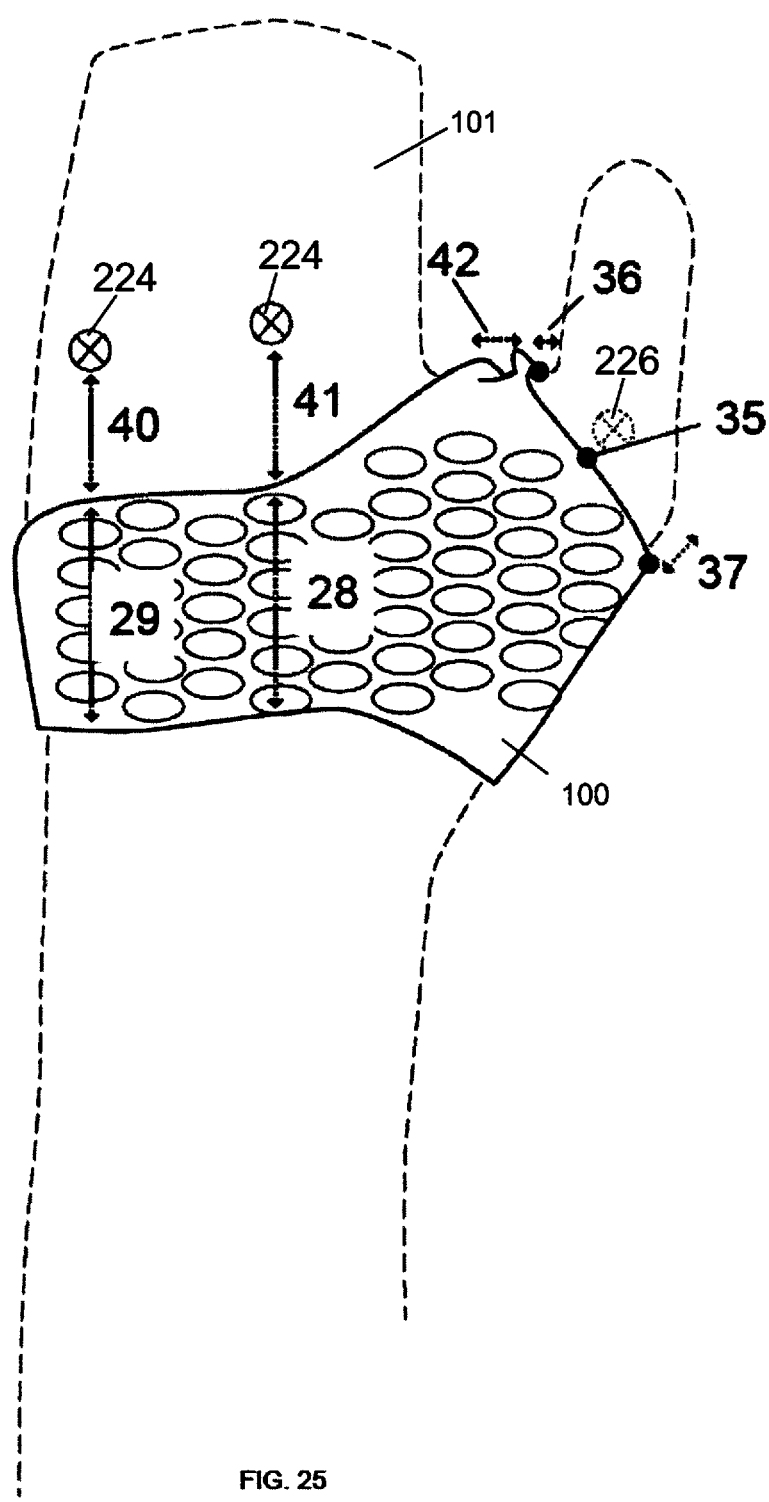
FIG. 25 illustrates a bottom view of a hand with hand brace design features.

With reference to FIG. 25, the low thumb point 35 on the palm side of the thumb can be on the inside of the hand 101 in the middle of the thumb. The distance from the low thumb point 35 on the palm portion of the brace 100 to a point on the hand 101 opposite the thumb MCP joint marking 226 can be about 1 mm-2 mm. The distance from the base of the thumb along the ridge of the skin formed by the thumb webbing to low thumb point 36 on the edge of the brace 100 can be about 4 mm-8 mm. A point 37 on the lateral side of hand below the thumb can be about 9 mm-13 mm proximal of thumb MCP joint 226. A point of the distal edge of the thumb portion of the brace 100 on lateral back of hand 101 that is intermediate between webbing and low thumb point from radial styloid to thumb MCP joint 226 can be a point from the thumb MCP joint 226 along a line towards the index finger MCP joint 224 and rotated between about 10 degrees and 20 degrees towards the wrist which can be a distance approximately equal to the radius of the thumb MCP joint 226 plus about a 2 mm-3 mm offset along the line that defines this point's position.

The edge flaring for low thumb on thumb opening can have a specific design that has a maximum flaring at the webbing falling off to minimum height about 0.65-0.85 of the distance to the opposite point on the lateral side of the thumb along the palm and about 0.2-0.3 times of the distance along the back of the hand. In an embodiment, the edge flaring for low thumb on thumb opening can have a max value=3.5 mm and a min value=1 mm. The edge flaring on distal extent of the lower back of hand portion of the brace can be the flaring along the distal extent of the brace below the side of the index finger. The edge flaring can extend about 15 mm-25 mm along the back of the hand and palm.

High Thumb

In one embodiment with reference to FIG. 26, an embodiment of the brace that has a thumb section that extends higher along the thumb to a location between the metaphalangeal and interphalangeal joints to provide additional support and/or protection of the thumb. The extent along the thumb 39 can be approximately 0.2-0.8 times the distance between the thumb MCP joint 226 and the proximal interphalangeal MCP joint of the thumb. The edge flaring on the distal extent of the brace at the end of the thumb opening can be uniform and circumferential.

Clasp Assets

With reference to FIGS. 21 and 22, the placement of the positive asset 415 can be centered along the line of the band 457. The edges of the positive assets 415 can be parallel with the line of the band 457. In an embodiment, the band 457 can extend 5 mm beyond the center of the asset. The placement of remaining negative assets 415 which can be the holes which engage the hook 419 at the distal portion of the band 457 that are placed in positions to provide a range of regular band 457 tightness settings for the patient. In an embodiment, there can be about 5 holes 415 that are each given a different tightness setting with setting 1 being the tightest and setting 5 being the loosest. Setting 2 can be tighter than setting 3 and setting 4 can be tighter than setting 5. In an embodiment, 2 assets towards the wrist are offset below the center asset towards the base of the thumb and 2 assets are placed above central asset towards MCP joints. The offsets between the adjacent assets can be about 2 mm center to center in each respective direction.

Palm

With reference to FIG. 25, the width of the brace 100 of the palmar region at the index finger 28 can be about 60%-70% of the distance between the small finger MCP joint 224 and the ulnar styloid marker 230 in the coronal plane. The width of the brace 100 in the palmar region at small finger 29 can be about 30%-50% of the distance between the small finger MCP joint 224 and the ulnar styloid marker 230 in the coronal plane. In an embodiment, the width of the brace 100 at the palmar region at small finger 29 can be about 30-40 mm. The distal edge at the small finger can be relative to the inside of the MCP joint and the distal edge at the middle finger can be relative to the inside of the MCP joint.

Across Palm to Back of Hand Thumb Bridge

With reference to FIG. 25, the region across the palm to the back of the hand 101 thumb bridge region can have a determined width 42 at its narrowest point that can be about 5 mm-20 mm. This material can span the webbing and can have a predetermined distance from the thumb 36 that is about 1-40 mm.

Button (for Separable Band)

In an embodiment as shown in FIG. 22, the proximal end of the band 457 can include a coupling that is attached to the brace. The coupling can include a cylindrical portion 456 having a diameter of about 3-7 mm or 5 mm and a height of about 1-4 mm. The diameter of the button head 458 of the coupling can be about 2-6 mm. The button head 458 height can be about 1-2 mm.

Slot for Attaching Band

In an embodiment, the beam width can be about 2-4 mm or 3 mm and the length of the beam can be about 8-12 mm or 10 mm. The receptacle hole diameter can be about 2-4 mm or 3 mm and the entry hole diameter can be about 6-10 mm or 8 mm. This structure is similar to the slot structure shown on the small finger side of the brace in FIGS. 20 and 23 and is substantially similar to the slot structure shown in FIG. 7 and described above.

Male Shape for Clasp of Band

With reference to FIG. 22, the male shape 419 is the protrusion on the bottom surface at the distal end of the band 457 that is used to connect the band 457 to a portion of the brace 100. The neck 419 can be about 1-3 mm or 2 mm and the width at the bottom of the clasp can be about 2-5 mm or 3.5 mm. The angle of the lip of the clasp 419 can be about 30-60 or 45 degrees.

Female Shape for Clasp of Band

With reference to FIG. 20, the female shape of the recesses 415 in the brace 100 that can be coupled to the male shape 419 of the clasp 457, can have a width at the top surface that is about 3-6 mm or 4.5 mm, a width at the bottom surface that is about 6-10 mm or 8 mm and a length that is about 4-7 mm or 5.5 mm. The angle of the inner surface of the female clasp 415 can be about 30-60 or 45 degrees.

Offsets from Scan Data to Brace Surface

The brace 100 can be designed to have an inner surface that corresponds to the scan data for the patient. In order to provide a comfortable fit for the patient, the inner surface of the brace 100 can be designed to be slightly larger or smaller than the surface data for the patient. Different portions of the brace 100 can have different offsets between the surface data and the inner brace design data. Different portions of the brace 100 can have different offsets so that some portions of the brace 100 are designed with an inner surface that more closely matches the surface data for the patient and other portions of the brace 100 that have an inner surface that are further offset away from or inward from the surface data for the patient. In an embodiment, a positive offset indicates a portion of the brace 100 that is expanded away from the surface data so that there is more room between the inner surface of the brace 100 and the skin of the patient. A negative offset indicates that a portion of the brace 100 is smaller than the surface data so these regions of the brace 100 are compressed against the patient.

In an embodiment, the palmar side compression can have a maximum offset and a taper. In an embodiment, the offset can be a linear taper of about 1 mm-6 mm offset on side of the palm extending as far as the brace 100 extends on the back of the hand. The offsets can be described in terms of their maximum offset, over what area the offset is at a maximum value, and the distance where the values return to nominal, which we call the falloff. In other embodiments, the offset can be about 7% of the width from the small finger MCP joint 224 to the index MCP joint 224.

The thumb hole can be designed to allow free insertion and removal. Thus, the thumb portion must have an inner surface that is larger than the largest cross section of the thumb. Frequently, the largest cross section of the thumb is the MCP joint area. In an embodiment, the inner surface of the brace 100 surrounding the thumb can correspond to the perimeter of the thumb MCP joint with an additional distance around the MCP joint perimeter. In an embodiment the additional distance can be about 0.5-1.5 mm. By providing a brace 100 with a thumb hole that is slightly larger than the largest cross section, the thumb will slide easily in and out of the brace 100 while still providing a close fit that provides support and protection.

The inner surface of the lateral back of the hand portion of the brace 100 can be designed based upon an inflation in area medial of the edge of the brace 100, pulling up the edge. In an embodiment the additional distance can be about 1.0-3.0 mm. By providing a brace 100 with a lateral back of the hand 101 that is slightly larger than the back of hand surface data, the hand 101 will slide easily in and out of the brace 100 while still providing a close fit.

In other embodiments, the inventive brace 100 can have additional offsets. The first offset can be a negative offset (inward from the scan data) over the thenar eminence. The max offset is 4 mm the falloff is 30% the length of the first metacarpal. We also added an offset on the medial back of hand under the edge of the brace 100, which performs the same function as the offset on the lateral back of hand 101. The same ranges can be used.

Serial Number

In an embodiment, the serial number of the brace 100 can be part of the brace design. The placement of the serial number can be centered around a point 40 mm along a vector running along the vertical axis of the arm side of the brace 100 from the band 457 beginning. The text height can be about 4 mm and the text spacing can be about 4 mm. In other embodiments any other text size and spacing can be used.

Fenestrations

In an embodiment, the fenestrations can be about 1-4 mm in width and/or length. The mechanical assets and webbing of the brace 100 can be designed without fenestrations.

Fabrication Process

With reference to FIG. 25, a flowchart of the process steps for fabricating a brace is illustrated. As discussed above, the patient's hand can be marked 661 with any type of marking device such as a sticker or ink that can be photographed. The markings can indicate a surface location of anatomical features such as the finger MCP joints, radial styloid, and the ulnar styloid. The markings can also indicate the location of the injury, edges of the brace, seams of the modular brace, seams of the brace pieces, sensitive areas, locations of stitches, and other body features. The patient's hand and arm can be illuminated with IR or visible light in a pattern such as dots, lines, grids or any other plurality of light points 663. The hand can be photographed with IR and/or visible light cameras as described 665. From the photographic data, the surface data for the patient's hand can be obtained 667. In other embodiments the hand may not be illuminated with an IR or visible light pattern and the surface data can be obtained by the natural markings on the patient's skin.

The surface data can be used to design interior surfaces of a brace 669. With the hand surface data and additional information about the hand injury, the wrist brace can be designed to prevent specific types of movements 671. The brace design can also be modified to include additional marking and mounting features 673. The markings added to the brace design can include information, ornamental designs, injury locations, etc. The mounts added to the brace can include device mounts and instrumentation mounts. If the hand changes in size but remains injured, a new brace may need to be fabricated to provide the required support and restricted movement 675. The described process can be repeated to fabricate a new brace based upon new photographs of the patient's hand.

After the brace or device is designed with the adjustable couplings incorporated, the brace design data is transmitted to a three dimensional fabrication machine that constructs the brace. In an embodiment, the three dimensional fabrication machine is rapid prototyping, rapid manufacturing, layered manufacturing, 3D printing, laser sintering, and electron beam melting (EBM), fused material deposition (FDM), CNC, etc. The fabrication machine produces a three dimensional single or multiple piece structure that can be plastic, metal or a mix of different materials by forming planar cross section layers of the structure on a previously formed planar cross section layers. This layered fabrication process is continued from one end of the structure to the opposite end until the structure is completely fabricated.

In order to efficiently produce the described devices, it can be desirable to simultaneously produce as many component parts as possible. Many fabrication machines can produce parts fitting within a specific volume in a predetermined period of time. For example, a brace can fit around the torso of a patient and have a large space in the center. This brace can be made, but it will only make one device. In order to improve the efficiency, the brace can be designed as multiple pieces that are later coupled or fused together. Rather than making a single brace with the large open center area, the described fabrication methods can be used to simultaneously produce components for two or more braces that occupy the same specific volume as a single piece brace. The cost of fabrication using a three dimensional fabrication machine can be proportional to the amount of time required to print the components rather than the raw material costs. The print time can be minimized by placing as many component cross sections into the print area as possible. If a back or limb brace normally has a large open center area the print cost efficiency can be poor. However, if the brace is a modular design, the modular section pieces can be fabricated in a more efficient manner. For example, multiple modular section pieces can be fabricated simultaneously with the convex surfaces of a first section piece adjacent to concave surfaces of another section piece. By laying out the components in an efficient production manner for fabrication by an additive material machine, the cost of fabrication can be significantly reduced. The components can then be assembled and coupled or fused together to form the brace. In an embodiment, the inner surface of the brace can be manufactured with a high resolution so that the inner surface is very smooth.

When the brace is fabricated using a three dimensional printing machine, the brace is formed by depositing a plurality of parallel planar layers of material with each layer fused to the adjacent layer. Each layer of material used to form the brace can have a predetermined and uniform thickness. In order to optimize the efficiency of the brace fabrication, it can be desirable to minimize the number of parallel planar layers used to create the brace. This minimizes the number of layers that are formed to create the brace and optimizes the fabrication efficiency. In an embodiment, the brace design information can be placed in a virtual box having square corners. The parallel planar layers formed to create the brace can be perpendicular to the shortest dimension of the brace which can be the thickness of the box.

After the brace or device is designed with the adjustable couplings incorporated, the brace design data is transmitted to a three dimensional fabrication machine that constructs the brace. In an embodiment, the three dimensional fabrication machine is rapid prototyping, rapid manufacturing, layered manufacturing, 3D printing, laser sintering, and electron beam melting (EBM), fused material deposition (FDM), CNC, etc. The fabrication machine produces a three dimensional single or multiple piece structure that can be plastic, metal or a mix of different materials by forming planar cross section layers of the structure on a previously formed planar cross section layers. This layered fabrication process is continued from one end of the structure to the opposite end until the structure is completely fabricated.

After the brace shell has been formed, additional processing can be performed on the inner surface to increase the smoothness. The inner surface can be tumbled, sanded, polished, or other processes can be used to create the smooth inner surfaces of the brace. These processes can be performed by hand or by a machine. In other embodiments, a filler material can be deposited on the inner surface of the brace shell to create a smooth surface or enhance the surface properties by increasing smoothness and hardness. For example, the inner surface may be painted and the paint may fill the uneven surfaces and dry to a smooth surface. Alternatively, the inner surface can be heated to cause the brace material to reflow and create a smooth inner surface.

The use of a photographic process has many advantages over other surface scanning technologies such as laser scanning. The process for transposing the locations of features from the patient to the brace or device is simplified because the doctor can apply location marks to the patient directly or on a form fitting covering. Thus, the locations of the features are much more likely to be accurately placed on the final product. The equipment costs are also reduced because the digital cameras, computers and electronic memory are inexpensive. The photographic equipment is also portable, so it can be easily transported to patient's location. The digital data can then be transmitted electronically to a fabrication machine located at a guild. Alternatively, the digital device data can be recorded onto a disk and transmitted to the fabrication machine.

The present disclosure, in various embodiments, includes components, methods, processes, systems and/or apparatus substantially as depicted and described herein, including various embodiments, subcombinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation. Rather, as the following claims reflect, inventive aspects lie in less than all features of any single foregoing disclosed embodiment.

What is claimed is:

1. A method for automatically creating a design for a conformal hand brace comprising:
   placing a plurality of markers on a hand of a patient;
   placing the hand of the patient between a plurality of cameras;
   simultaneously taking photographs of the markers and the hand of the patient with the plurality of cameras;
   calculating a digital representation of the hand from the photographs;
   storing a digital representation of the hand in a computer memory; and
   automatically designing the conformal hand brace based upon the digital representation of the hand and locations of the markers with a computer processor, the conformal hand brace having a palm region and a thumb region;
   wherein the conformal hand brace includes inner surface regions that inherently correspond to the digital representation of the hand wherein the inner surface regions are offset from the digital representation of the hand and a width of the palm region aligned a small finger of the patient is 30%-50% of the distance between a small finger metacarpophalangeal (MCP) joint and an ulnar styloid of the hand of the patient in a coronal plane.

2. The method of claim 1 wherein a width of the palmar region aligned an index finger of the patient is 60%-70% of the distance between a small finger metacarpophalangeal (MCP) joint and an ulnar styloid of the hand of the patient in a coronal plane.

3. The method of claim 1 wherein a width of the thumb region of the brace in the coronal plane is 45% to 65% of the distance between a radial styloid and a middle finger metacarpophalangeal (MCP) joint of the hand of the patient in a coronal plane.

4. The method of claim 1 wherein the markers are placed on a radial styloid or an ulnar styloid of the hand.

5. The method of claim 1 wherein the markers are placed on one or more metacarpophalangeal (MCP) joints of the hand.

6. The method of claim 1 wherein the conformal hand brace has one or more inner surface regions that are offset from the digital representation of the hand in a negative direction that compresses the hand.

7. The method of claim 6 wherein the one or more inner surface regions of the conformal hand brace that are offset from the digital representation of the hand includes a region over the thenar eminence of the hand in a negative direction towards the hand.

8. The method of claim 1 wherein the brace design has one or more inner surface regions of the conformal hand brace that are offset from the digital representation of the hand in a positive direction away from a lateral back portion of the hand.

9. The method of claim 1 wherein the brace design has one or more inner surface regions of the conformal hand brace that are offset from the digital representation of the hand in a positive direction away from a medial back portion of the hand.

10. A method for automatically creating a design for a conformal hand brace comprising:
simultaneously taking photographs of a hand of the patient with a plurality of cameras;
calculating a digital representation of the hand from the photographs; and
automatically designing the conformal hand brace based upon the digital representation of the hand with a computer processor, the conformal hand brace having a palm region and a thumb region;
wherein the conformal hand brace includes a plurality of inner surface regions that correspond to the digital representation of the hand and a width of the thumb region of the brace in the coronal plane is 45% to 65% of the distance between a radial styloid and a middle finger metacarpophalangeal (MCP) joint of the hand of the patient in a coronal plane.

11. The method of claim 10 wherein a width of the palmar region aligned an index finger of the patient is 60%-70% of the distance between a small finger metacarpophalangeal (MCP) joint and an ulnar styloid of the hand of the patient in a coronal plane.

12. The method of claim 10 wherein a width of the palm region aligned a small finger of the patient is 30%-50% of the distance between a small finger metacarpophalangeal (MCP) joint and an ulnar styloid of the hand of the patient in a coronal plane.

13. The method of claim 10 further comprising:
placing a marker of a radial styloid or an ulnar styloid of the hand prior to taking of photographs of the hand.

14. The method of claim 10 further comprising:
placing a marker of one or more metacarpophalangeal (MCP) joints of the hand prior to taking of photographs of the hand.

15. The method of claim 10 wherein the conformal hand brace has one or more inner surface regions that are offset from the digital representation of the hand in a negative direction that compresses the hand.

16. The method of claim 15 wherein the one or more inner surface regions of the conformal hand brace that are offset from the digital representation of the hand includes a region over the thenar eminence of the hand in a negative direction towards the hand.

17. The method of claim 10 wherein the brace design has one or more inner surface regions of the conformal hand brace that are offset from the digital representation of the hand in a positive direction away from a lateral back portion of the hand.

18. The method of claim 10 wherein the brace design has one or more inner surface regions of the conformal hand brace that are offset from the digital representation of the hand in a positive direction away from a medial back portion of the hand.

* * * * *